United States Patent
Weissleder et al.

(10) Patent No.: US 9,958,416 B2
(45) Date of Patent: May 1, 2018

(54) ANALYTE DETECTION USING MAGNETIC HALL EFFECT

(71) Applicant: The General Hospital Corporation, Boston, MA (US)

(72) Inventors: Ralph Weissleder, Peabody, MA (US); Hakho Lee, Acton, MA (US); David Issadore, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days. days.

(21) Appl. No.: 14/360,090

(22) PCT Filed: Nov. 21, 2012

(86) PCT No.: PCT/US2012/066283
§ 371 (c)(1),
(2) Date: May 22, 2014

(87) PCT Pub. No.: WO2013/078332
PCT Pub. Date: May 30, 2013

(65) Prior Publication Data
US 2014/0295460 A1 Oct. 2, 2014

Related U.S. Application Data

(60) Provisional application No. 61/563,337, filed on Nov. 23, 2011.

(51) Int. Cl.
*G01N 27/74* (2006.01)
*G01N 33/53* (2006.01)
(Continued)

(52) U.S. Cl.
CPC ....... *G01N 27/745* (2013.01); *G01N 33/5308* (2013.01); *G01N 33/56911* (2013.01);
(Continued)

(58) Field of Classification Search
None
See application file for complete search history.

(56) References Cited

U.S. PATENT DOCUMENTS 5,811,844 A * 9/1998 Kuo ................... H01L 29/7785
257/194
7,179,383 B1 2/2007 Porter et al.
(Continued)

FOREIGN PATENT DOCUMENTS

RU          2415432       3/2011
WO     WO 2000/061191    10/2000

OTHER PUBLICATIONS

Aytur et al "A novel magnetic bead bioassay platform using a microchip-based sensor for infections disease diagnosis" Journal of Immunological Methods, 2006, 314:21-29.*
(Continued)

*Primary Examiner* — Betty J Forman
(74) *Attorney, Agent, or Firm* — Fish & Richardson P.C.

(57) ABSTRACT

Determining a presence of a target analyte in a fluid sample includes mixing multiple magnetic particles with the fluid sample, in which the magnetic particles are each bound to one or more binding moieties that specifically bind to the target analyte, flowing the fluid sample containing the magnetic particles through a fluidic channel, exposing the fluid sample in the fluidic channel to a magnetic field, measuring a signal from a Hall effect sensor while the fluid sample flows through the fluidic channel, and determining whether the target analyte is present in the fluid sample when the measured signal is in a first range of values.

13 Claims, 19 Drawing Sheets

(51) Int. Cl.
G01N 33/569 (2006.01)
G01N 33/68 (2006.01)
G01N 33/543 (2006.01)

(52) U.S. Cl.
CPC . G01N 33/56916 (2013.01); G01N 33/56938 (2013.01); G01N 33/56966 (2013.01); G01N 33/68 (2013.01); G01N 33/54373 (2013.01); Y10T 436/143333 (2015.01)

(56) References Cited

U.S. PATENT DOCUMENTS

| | | | |
|---|---|---|---|
| 2003/0092029 | A1 | 5/2003 | Josephson et al. |
| 2003/0124194 | A1 | 7/2003 | Gaw et al. |
| 2006/0269965 | A1 | 11/2006 | Josephson et al. |
| 2007/0057748 | A1* | 3/2007 | Lean ............... B03C 5/028 333/157 |
| 2008/0314749 | A1* | 12/2008 | Johnson ........... B01L 3/50273 204/450 |
| 2010/0102358 | A1 | 4/2010 | Lanzieri et al. |
| 2011/0035176 | A1* | 2/2011 | Gao ..................... 702/117 |
| 2011/0091987 | A1 | 4/2011 | Weissleder et al. |
| 2011/0277540 | A1 | 11/2011 | Ioppolo et al. |

OTHER PUBLICATIONS

Loureiro et al "Toward a magnetoresisitve chip cytometer: Integrated detection of magnetic beads flowing at cm/s velocities in microfluidic channels" Applied Physics Letters, 2009, 95: 034104-1-034104-3.*
Hse et al "Microvortex for focusing, guiding and sorting of particles" Lab on a Chip, 2008, 8: 2128-2134.*
International Preliminary Report on Patentability in International Application No. PCT/US2012/066283, dated Jun. 5, 2014, 5 pages.
Adams et al., "Multitarget magnetic activated cell sorter," Proc. Natl. Acad. Sci. USA, 105:18165-18170 (2008).
Arias et al., "Unmet needs and prospects for oritavancin in the management of vancomycin-resistant enterococcal infections," Clin Infect Dis., 54(Suppl 3):S233-8 (2012).
Batt, "Materials science. Food pathogen detection," Science, 316:1579-80 (2007).
Bendall et al., "Single-cell mass cytometry of differential immune and drug responses across a human hematopoietic continuum," Science, 332:687-696 (2011) (Author Manuscript).
Bishara et al., "Holographic pixel super-resolution in portable lensless on-chip microscopy using a fiber-optic array," Lab Chip., 11:1276-1279 (2011) (Author Manuscript).
Brennan et al., "Antibody-based proteomics: fast-tracking molecular diagnostics in oncology," Nat. Rev. Cancer, 10:605-617 (2010).
Budin et al., "A magnetic Gram stain for bacterial detection," Angew Chem Int Ed Engl., 51:7752-7755 (2012) (Author Manuscript).
Chin et al., "Microfluidics-based diagnostics of infectious diseases in the developing world," Nat Med., 17:1015-9 (2011).
Chung et al., "Ubiquitous detection of gram-positive bacteria with bioorthogonal magnetofluorescent nanoparticles," ACS Nano., 5:8834-41 (2011).
Ejsing et al., "Planar Hall effect sensor for magnetic micro-and nanobead detection," Appl. Phys. Lett., 84:4729-4731 (2004).
Ellerbee et al., "Quantifying colorimetric assays in paper-based microfluidic devices by measuring the transmission of light through paper," Anal. Chem., 81:8447-8452 (2009).
Enserink, "Anthrax. Biodefense hampered by inadequate tests," Science, 294:1266-7 (2001).
Etzioni et al., "The case for early detection," Nat. Rev. Cancer, 3:243-252 (2003).
Fan et al., "Integrated barcode chips for rapid, multiplexed analysis of proteins in microliter quantities of blood," Nat. Biotechnol., 26:1373-1378 (2008).
Gaster et al., "Matrix-insensitive protein assays push the limits of biosensors in medicine," Nat. Med., 15:1327-1332 (2009) (Author Manuscript).
Giljohann and Mirkin, "Drivers of biodiagnostic development," Nature, 462(7272):461-464 (2009) (Author Manuscript).
Gu et al., "Nanogap field-effect transistor biosensors for electrical detection of avian influenza," Small., 5:2407-2412 (2009).
Haun et al., "Bioorthogonal chemistry amplifies nanoparticle binding and enhances the sensitivity of cell detection," Nat. Nanotechnol., 5:660-665 (2010) (Author Manuscript).
Haun et al., "Micro-NMR for rapid molecular analysis of human tumor samples," Sci Transl Med., 3:71ra16 (2011).
Howell, Jr. et al., "Two simple and rugged designs for creating micro fluidic sheath flow," Lab Chip, 8:1097-1103 (2008).
Issadore et al., "Ultrasensitive clinical enumeration of rare cells ex vivo using a micro-hall detector," Sci Transl Med, 4:141ra92 (2012).
Josephson et al., "High-efficiency intracellular magnetic labeling with novel superparamagnetic-Tat peptide conjugates," Bioconjug. Chem., 10(2):186-91 (1999).
Kamal et al., "A high-affinity conformation of Hsp90 confers tumour selectivity on Hsp90 inhibitors," Nature, 425:407-410 (2003).
Lee et al., "Chip—NMR biosensor for detection and molecular analysis of cells," Nat. Med., 14:869-874 (2008) (Author Manuscript).
Lee et al., "Ultrasensitive detection of bacteria using core-shell nanoparticles and an NMR-filter system." Angew. Chem. Int. Ed. Engl., 48:5657-5660 (2009) (Author Manuscript).
Liong et al., "Specific pathogen detection using bioorthogonal chemistry and diagnostic magnetic resonance," Bioconjug Chem., 22:2390-2394 (2011) (Author Manuscript).
Loureiro et al., "Magnetoresistive chip cytometer," Lab Chip 11:2255-2261 (2011).
Menichetti, "Current and emerging serious Gram-positive infections," Clin Microbiol Infect., 11(Suppl 3):22-8 (2005).
Nagrath et al., "Isolation of rare circulating tumour cells in cancer patients by microchip technology," Nature, 450:1235-1239 (2007) (Author Manuscript).
Phillips et al., "Rapid and efficient identification of bacteria using gold-nanoparticle-poly(para-phenyleneethynylene) constructs," Angew Chem Int Ed Engl., 47:2590-4 (2008).
Popović, "Hall effect devices," Institute of Physics, London, England, pp. 236-314 (2004).
Shevkoplyas et al., "The force acting on a superparamagnetic bead due to an applied magnetic field," Lab Chip, 7:1294-1302 (2007).
Sorger, "Microfluidics closes in on point-of-care assays," Nat. Biotechnol., 26:1345-1346 (2008).
Sun et al., "High speed multi-frequency impedance analysis of single particles in a microfluidic cytometer using maximum length sequences," Lab Chip., 7:1034-1040 (2007).
Weigl et al., "Towards non- and minimally instrumented, microfluidics-based diagnostic devices," Lab Chip, 8:1999-2014 (2008) (Author Manuscript).
Woodford and Livermore, "Infections caused by Gram-positive bacteria: a review of the global challenge," J Infect., 59(Suppl 1):S4-S16 (2009).
Xuan et al., "Particle focusing in microfluidic devices," Microfluid Nanofluid, 9:1-16 (2010).
Yang et al., "Association with HSP90 inhibits Cbl-mediated downregulation of mutant epidermal growth factor receptors," Cancer Res., 66:6990-6997 (2006).
Yang et al., "Microfabrication and test of a three-dimensional polymer hydro-focusing unit for flow cytometry applications Original," Sensors and Actuators A: Physical, 118:259-267 (2005).
Zhao et al., "A rapid bioassay for single bacterial cell quantitation using bioconjugated nanoparticles," Proc Natl Acad Sci U S A, 101:15027-32 (2004).
International Search Report and Written Opinion dated Feb. 28, 2013 in international application No. PCT/US2012/066283, 6 pgs.

* cited by examiner

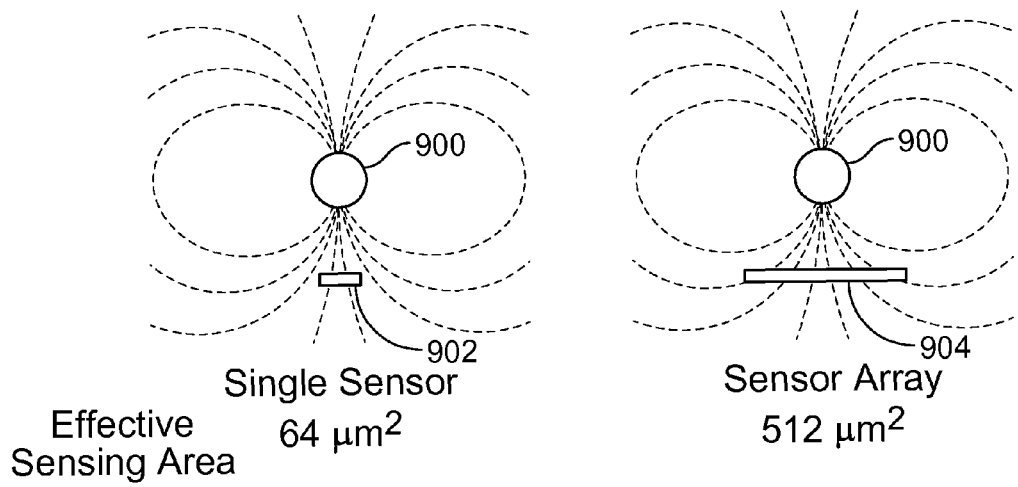
Effective Sensing Area — Single Sensor 64 μm² 
FIG. 8
Sensor Array 512 μm²
FIG. 9
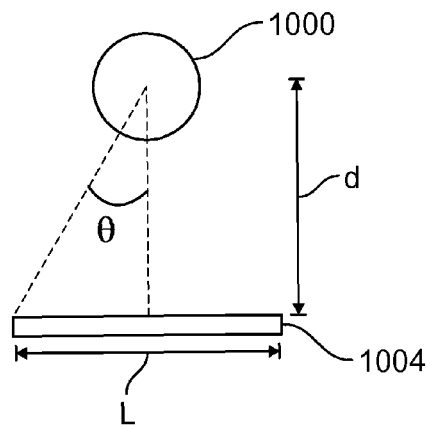
FIG. 10A
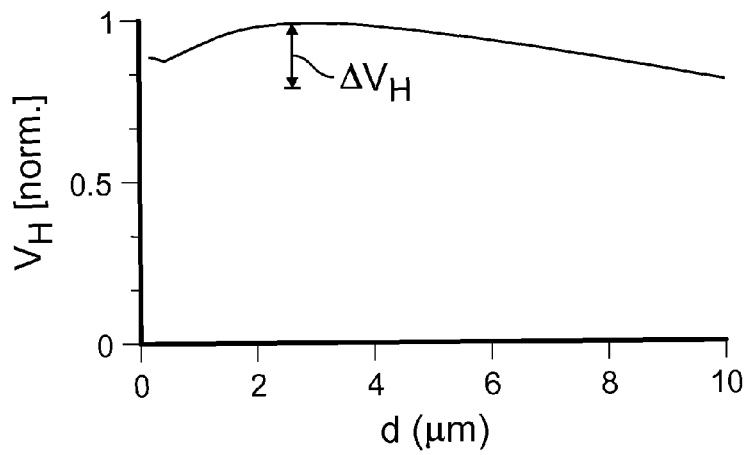
FIG. 10B

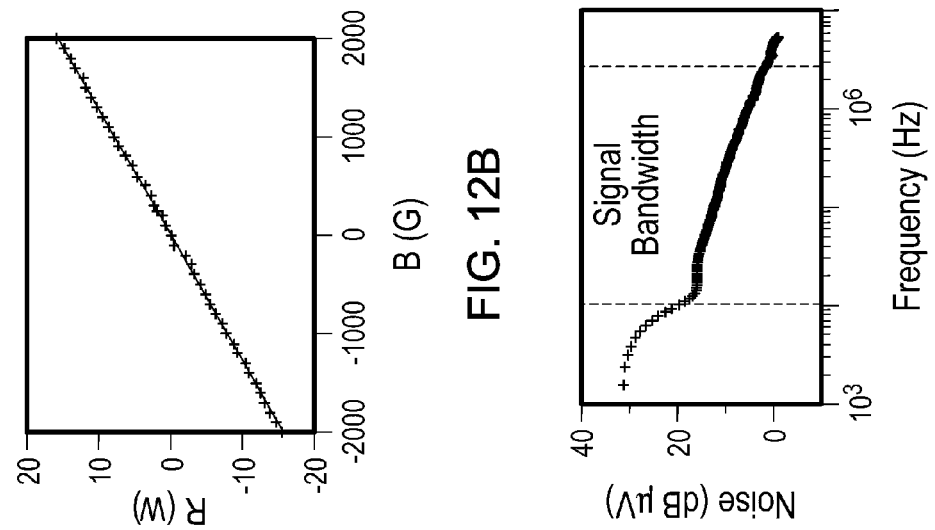
FIG. 12B
FIG. 12C
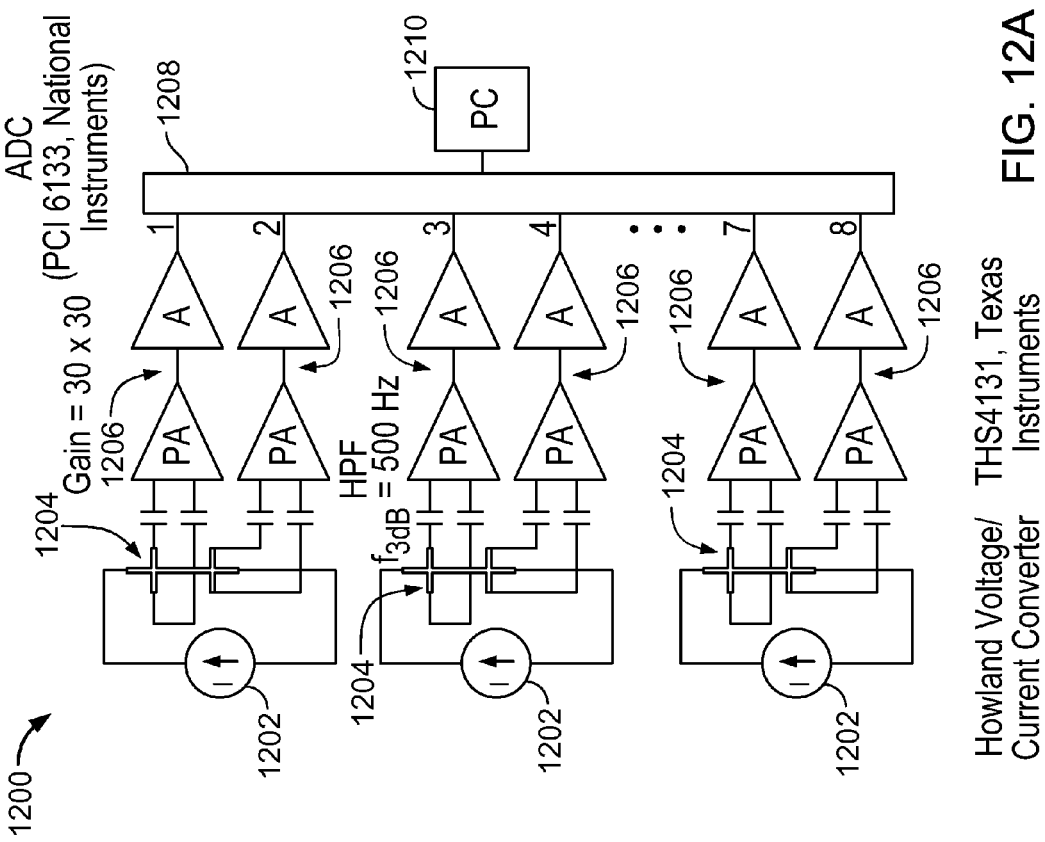
FIG. 12A

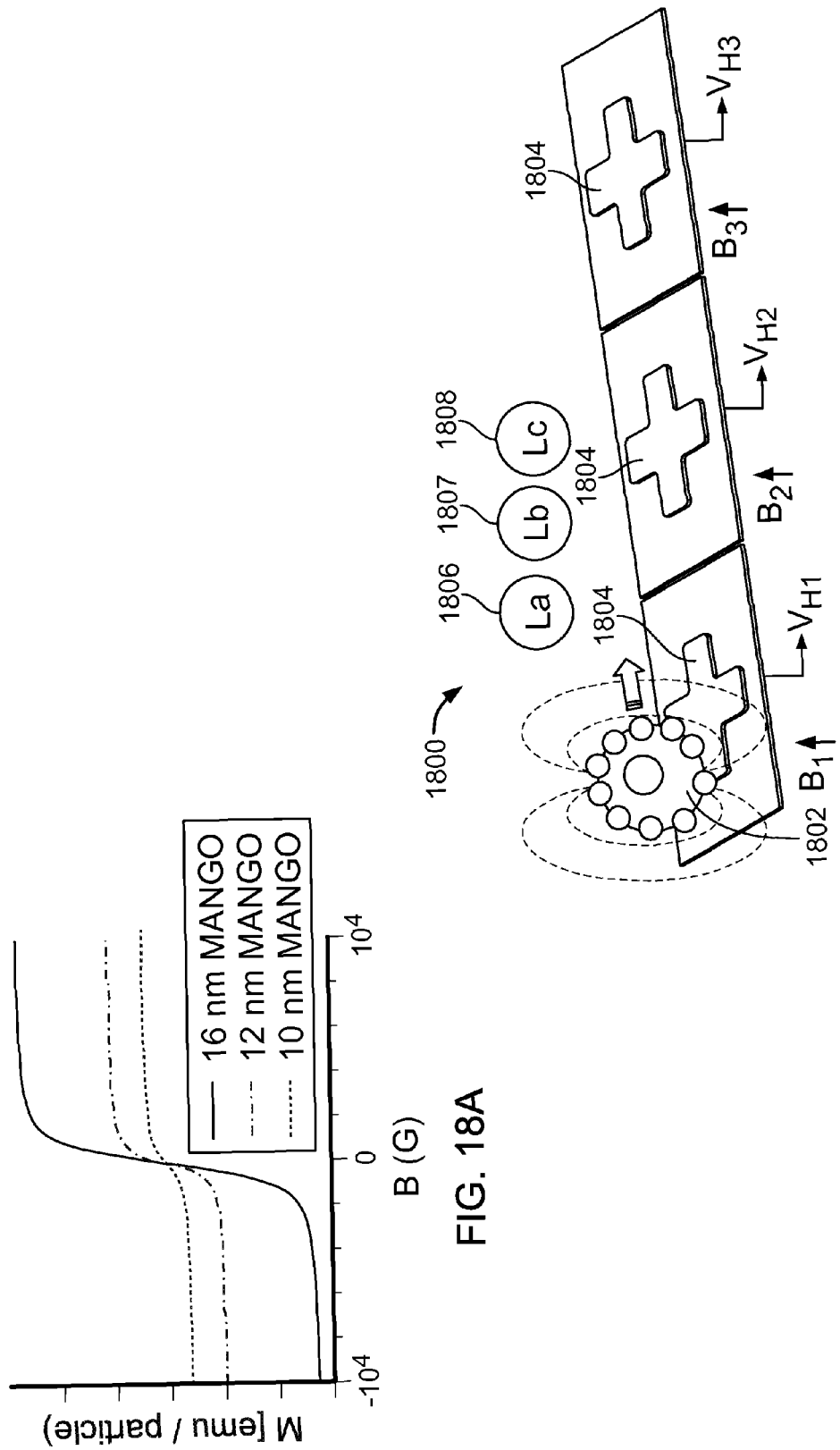

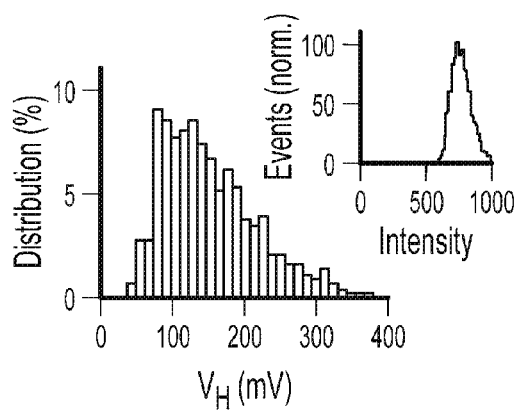 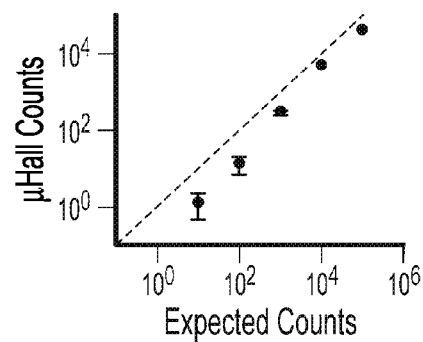
FIG. 22A　　　　　　　　　　FIG. 22B
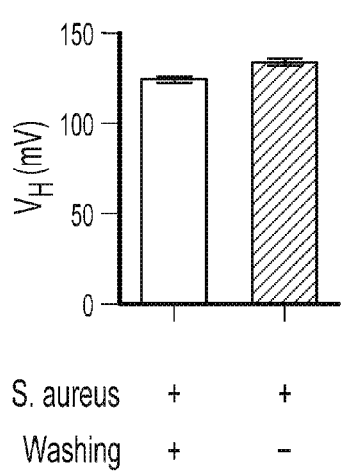 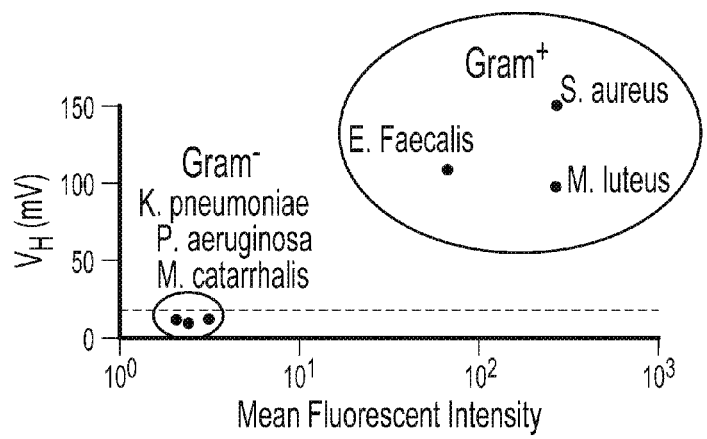
FIG. 22C　　　　　　　　　　FIG. 22D

US 9,958,416 B2

ANALYTE DETECTION USING MAGNETIC HALL EFFECT

PRIORITY CLAIM

This application is a 35 U.S.C. § 371 national stage application of International Application No. PCT/US2012/066283, filed Nov. 21, 2012, which claims the benefit of U.S. Provisional Patent Application No. 61/563,337, filed Nov. 23, 2011. The entire contents of the foregoing are incorporated herein by reference.

STATEMENT AS TO FEDERALLY SPONSORED RESEARCH

Funding for the work described herein was provided, at least in part, through National Institute of Health Grants R01-EB0044626, R01-EB010011, T32 grant T32CA79443, P50 grant P50CA86355, each of which is administered by the federal government, which has certain rights in the invention.

BACKGROUND

A number of platforms to detect molecular biomarkers have been developed, creating tools to probe complex biological systems. These approaches have been based on various sensing techniques including nuclear magnetic relaxometry, mass spectrometry, holographic imaging, fluorescence detection, microfluidic sorting and sensors based on surface plasmon resonance, colorimetry, magnetoresistance, electrical impedance, and field-effect gating. It remains challenging, however, to resolve sparse cells or scant biomarkers in native samples that are abundant with host cells. Accordingly, extensive sample preparation and purification processes may need to be employed, which can lead to the loss of target cells and/or the decay of molecular biomarkers, thus inhibiting routine clinical use.

SUMMARY

The subject matter of the present disclosure relates to analyte detection using the magnetic Hall effect.

Various aspects of the invention are summarized as follows. In general, in a first aspect, the subject matter of the disclosure can be embodied in target analyte detection devices and systems that include or consist of a substrate including a Hall effect sensor, a fluidic channel, e.g., a microfluidic channel, arranged on a surface of the substrate and extending over a detection area of the Hall effect sensor, a magnet arranged to generate a magnetic field in the fluidic channel, and control electronics coupled to the Hall effect sensor, in which the control electronics are configured to cause the device to: detect a signal from the Hall effect sensor and determine a presence of a target analyte in the fluidic channel based on the signal.

Implementations of the devices and systems can include one or more of the following features and/or features of other aspects. For example, the substrate further can include a pseudomorphic high electron mobility transistor (PHEMT) heterostructure.

In some implementations, the Hall effect sensor includes a first pair of electrodes and a second pair of electrodes, in which the electronic processor is configured to: detect a signal from the first pair of electrodes, and supply current to the Hall effect sensor through the second pair of electrodes.

In some implementations, the substrate further includes an insulating layer sandwiched between the Hall effect sensor and the fluidic channel. The insulating layer can include, e.g., one or more of an $Al_2O_3$ layer, a $Si_3N_4$ layer, and a $SiO_2$ layer.

In some implementations, the device further includes polydimethylsiloxane (PDMS) arranged on a surface of the substrate and configured to define boundaries of the fluidic channel.

In some implementations, a top surface of the fluidic channel includes multiple flow focusing structures. Each of the flow focusing structures can include one or more walls, e.g., in the shape of a line at an angle to the direction of flow in the channel or in the shape of a chevron pattern.

In some implementations, the fluidic channel includes one or more of a first input port to receive a first fluid sample at a first end of the fluidic channel, a second input port to receive a sheath fluid at the first end of the fluidic channel, and a third input port to receive the sheath fluid at the first end of the fluidic channel, in which the second input port and the third input port are positioned on opposite sides of the first input port to enable the formation of a sheath flow of the second fluid around the first fluid.

In some implementations, the device further includes multiple Hall effect sensors arranged along a length of the fluidic channel. At least two of the Hall effect sensors can be coupled in series across a width of the fluidic channel.

The devices and systems can also include, in some implementations, multiple fluidic channels on the substrate and multiple Hall effect sensors, in which each fluidic channel extends over a detection area of at least one Hall effect sensor.

In some implementations, the control electronics are further operable to determine one or more of a position, velocity, or size of the target analyte in the fluidic channel.

In some implementations, the control electronics are further operable to determine a presence of a second target analyte in the fluidic channel based on the measured signal.

In some implementations, the devices further include multiple Hall effect sensors, in which the control electronics are operable to: detect a signal from one or more of the Hall effect sensors; and determine a lateral position or a vertical position, or both, of the target analyte in the fluidic channel based on the signal.

In certain aspects, the subject matter of the present disclosure can be embodied in methods of determining a presence of a target analyte in a fluid sample, in which the method includes or consists of mixing a plurality of magnetic particles with the fluid sample, where the magnetic particles are each bound to one or more binding moieties that specifically bind to the target analyte, flowing the fluid sample containing the magnetic particles through a fluidic channel, exposing the fluid sample in the fluidic channel to a magnetic field, measuring a signal from a Hall effect sensor while the fluid sample flows through the fluidic channel, and determining whether the target analyte is present in the fluid sample when the measured signal is in a first range of values.

In some implementations, the signal is measured from two Hall effect sensors coupled in series.

The methods can include, in some implementations, determining one or more of a position, velocity, or size of the target analyte based on the measured signal, and/or determining a lateral position or vertical position, or both, of the target analyte in the fluidic channel based on the measured signal.

In some implementations, the methods can include flowing a sheath fluid into the fluidic channel to hydrodynamically focus the fluid sample in the fluidic channel.

In some implementations, the methods can include determining a presence of a second target analyte in the fluid sample when the measured signal is in a second range of values.

In certain aspects, the subject matter of the present disclosure can be embodied in methods of determining a presence of a target analyte in a fluid sample, in which the methods include mixing a plurality of magnetic particles with the fluid sample, where the magnetic particles are each bound to one or more binding moieties that specifically bind to the target analyte, flowing the fluid sample containing the magnetic particles into a plurality of fluidic channels, where each fluidic channel is positioned over one or more Hall effect sensors, exposing the fluid sample in the fluidic channels to a magnetic field, measuring signals from the one or more Hall effect sensors while the fluid sample flows through the fluidic channels, and determining whether the target analyte is present in the fluid sample based on the measured signals.

In some implementations, the target analyte can include one or more cells, polypeptides, or nucleic acids.

As used herein, "linked" means attached or bound by covalent bonds, non-covalent bonds, or other bonds, such as van der Waals forces.

As used herein, "specifically binds" means that one molecule, such as a binding moiety, e.g., an oligonucleotide or an antibody, binds preferentially to another molecule, such as a target molecule, e.g., a nucleic acid or a protein, in the presence of other molecules in a sample.

As used herein, "magnetic moment" is the tendency of a magnet to align with a magnetic field.

As used herein, a "binding moiety" is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be an oligonucleotide that hybridizes to a specific complementary nucleic acid target. In another example, the binding moiety can be an antibody directed toward an antigen or any protein-protein interaction. In another example, the binding moiety can be a polysaccharide that binds to a corresponding target. Other examples of binding moieties include polypeptide binding moieties. In certain implementations, the binding moieties can be designed or selected to serve, when bound to another binding moiety, as substrates for a target molecule, such as enzyme in solution.

A sheath flow of a sheath fluid "around" a first fluid means the sheath fluid either is limited to one or two sides of the first fluid flow, or the sheath fluid fully encloses and surrounds the first fluid flow on all sides, except for the inlet and outlet sides of the first fluid flow. The subject matter of the present disclosure offers a number of advantages in certain applications and implementations. For example, by laying out an array of sensors, one can detect target analytes independent of their lateral positions, allowing for the use of wider microfluidic channels with less stringent fluidic control. In addition, because arrays of Hall effect sensors integrate the overall magnetic flux from target analytes, accurate cellular profiling can be performed without being affected by the analyte size or position in flow.

The use of magnetic detection as described herein also enables measurements of target analytes in turbid samples, such as blood (e.g., whole blood, e.g., maternal blood), urine, cerebrospinal fluid, saliva, and sputum, thus decreasing the loss of rare cells, reducing the use of expensive sample processing equipment, and enabling the use of low cost, portable, point-of-care diagnostic devices. In some implementations, the Hall effect sensors described herein can be configured as part of a magnetic cytometer with multiple microfluidic channels, thus enabling high throughput analysis of fluid samples. The sensitivity of the Hall effect sensors also can be useful for detecting rare analytes (e.g., cancer cells) in fluid samples in applications such as monitoring disease diagnosis, progression or drug efficacy. In addition, by using immunomagnetic particles to label analytes of interest, it is possible in some implementations to detect a broad range of cellular markers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, drawings, and from the claims.

BRIEF DESCRIPTION OF THE DRAWINGS

FIG. 8 is a schematic cross-section of a magnetic target analyte and the effective sensing region of a single Hall effect sensor.

FIG. 9 is a schematic cross-section of a magnetic target analyte and the effective sensing region of multiple Hall effect sensors.

FIG. 10A is a schematic cross-section of a magnetic target analyte and the effective sensing area of a Hall effect sensor.

FIG. 10B is a plot of a simulation of an average output voltage from multiple Hall effect sensors versus a vertical distance from an effective sensing area of the Hall effect sensors.

FIG. 12A is a schematic of an example of control electronics used to operate Hall effect sensors in a magnetic cytometer.

FIG. 12B is a plot of output impedance of a Hall effect sensor versus applied magnetic field.

FIG. 12C is a plot of Hall effect sensor noise versus frequency.

FIG. 18A is a plot of magnetization response versus applied magnetic field for the different magnetic particles.

FIG. 18B is a schematic of an example of a magnetic cytometer for performing multiplexed detection measurements of a target analyte.

FIG. 22A is a plot of Hall voltage distribution.

FIG. 22B is a plot of bacterial counts using a magnetic cytometer versus expected bacterial counts.

FIG. 22C is a bar plot of Hall voltage with and without excess magnetic nanoparticles.

FIG. 22D is a plot of Hall voltage versus mean fluorescent intensity for different bacteria.

DETAILED DESCRIPTION

The present disclosure relates to devices for detecting analytes using the magnetic Hall effect and methods and applications for their use. The devices include one or more magnetic Hall effect sensors adjacent to a fluidic channel through which a sample fluid flows. The Hall effect sensors measure the magnetic moments of magnetic particles in the fluid sample, in which the magnetic particles may be bound to one or more target analytes. Based on a signal produced by the one or more Hall effect sensors in response to measuring the magnetic fields, the devices can be configured to determine various parameters, e.g., the presence, size, velocity, and/or type, of one or more target analytes of the same or different types. The devices can therefore be used for various applications including, among other things, flow cytometry of unprocessed biological samples such as blood (e.g., whole blood, e.g., maternal blood), urine, cerebrospinal fluid, saliva, and sputum.

Magnetic Cytometers Using One or More Hall Effect Sensors

Figure 1:
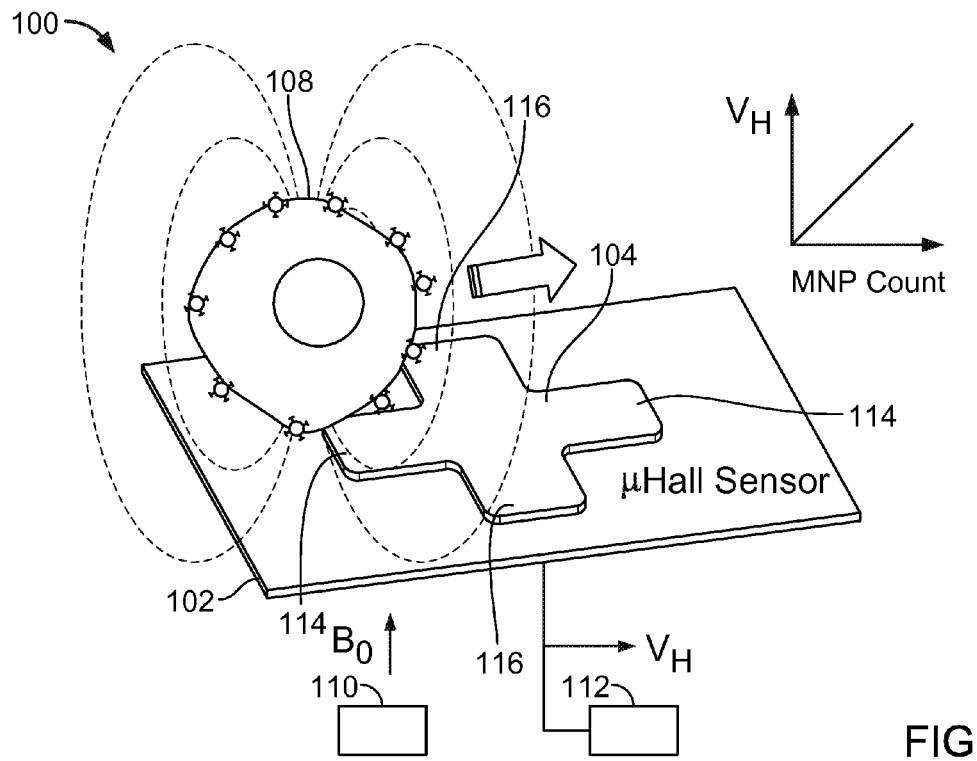
FIG. 1 is a schematic of an example of a magnetic cytometer as described herein.

FIG. 1 is a schematic of an example of a Hall effect sensing device (e.g., magnetic cytometer) 100 for detecting magnetic particles or magnetically-labeled analytes in a fluid sample. As shown in FIG. 1, the cytometer 100 includes a substrate 102, a Hall effect sensor 104, and a fluidic channel (not shown) through which a fluid sample containing a target analyte 108 flows. The cytometer 100 also includes a magnet 110 (e.g., a NdFeB permanent magnet having a size of about 1 cm³) positioned next to the substrate 102, where the magnet 110 creates a magnetic field $B_0$ extending into the fluidic channel. The Hall effect sensor 104 is electrically coupled to control electronics 112 through a first pair 114 of electrodes and a second pair of electrodes 116. The control electronics 112 supply current to the sensor 104 through the first pair 114 of electrodes and detect a voltage of the sensor 104 across the second pair 116 of electrodes.

The target analyte 108 can include a magnetic particle (e.g., magnetic nanoparticles) or a non-magnetic particle (e.g., a biological analyte of interest such as a nucleic acid (e.g., DNA, RNA), a polypeptide, bacteria, or a cell) to which other magnetic particles are attached, e.g., using a specific binding moiety, such as an antibody, binding ligand, or aptamer. During operation of the device 100, a fluid sample containing the target analyte 108 flows through the fluidic channel over a detection area of the Hall effect sensor 104. The fluid sample can be delivered using pressure based flow or gravity feed. For example, in some implementations, only a single source of positive pressure (e.g., at the inlet of the fluidic channel) or negative pressure (e.g., at the outlet of the fluidic channel) is necessary to generate the entire flow. For low-cost, point-of-care implementations, the flow can be driven by an inexpensive spring-loaded syringe or vacuum pack (further details on implementing a pressure source can be found, for example, in Weigl, B., Domingo, G., Labarre, P. & Gerlach, J., Towards non- and minimally instrumented, microfluidics-based diagnostic devices, Lab Chip 8, 1999-2014 (2008)).

In response to the external magnetic field $B_0$ provided by the magnet 110, each magnetic particle exposed to the field attains a magnetic moment $m_p$. For target analytes 108 to which multiple magnetic particles are attached, the total magnetic moment of the target analyte 108 is equal to the number of magnetic particles times the magnetic moment associated with each particle, $m=N \times m_p$. Various numbers of particles can be attached to a target analyte including, for example, N=1, 2, 10, 100, 500, 1000, 1500, 2000, 3500, 5000, 10,000 or more. Magnetic particles may have various magnetic moments depending on their size and construction. For example, the magnetic moment can be about $5 \times 10^{-5}$ A·μm$^2$, $1 \times 10^{-5}$ A·μm$^2$, $7 \times 10^{-6}$ A·μm$^2$, $3 \times 10^{-6}$ A·μm$^2$, $3 \times 10^{-7}$ A·μm$^2$ or less. There is no upper limit on detectable magnetic moments The Hall effect sensor 104 then detects the magnetic field emanating from the target analyte 108. That is, the Hall effect sensor 104 produces a voltage response across the second pair 116 of electrodes that is proportional to the magnetic field associated with each target analyte 108 traversing over a detection area of the Hall effect sensor 104.

Based on the measured voltage signal the control electronics 112 can be configured to determine various target analyte parameters, such as the presence, position, velocity, size, and/or type of the target analyte 108 in the fluid sample. For example, the control electronics 112 can be configured to identify the presence of a target analyte 108 if the measured voltage signal is above a specified threshold value. If the length over which the sensor can reliably detect the magnetic moment emanating from a target analyte is known, then the control electronics 112 also can be configured to determine a velocity of the target analyte 108 through the fluidic channel based on the time the measured voltage is above the specified threshold value. As indicated above, the target analyte can be bound to multiple magnetic particles. Accordingly, in some embodiments, larger target analytes may be bound to a greater number of magnetic particles than smaller analytes, thus producing a larger magnetic field. The magnitude of the Hall sensor output is thus, in some embodiments, proportional to the target analyte size and can, in some implementations, be used to differentiate different sized target analytes.

Using a Hall effect sensor to detect the local magnetic field emanating from the target analyte 108 can provide several advantages. For example, Hall effect sensors typically have a linear response over several orders of magnitude of the excitation magnetic field $B_0$ (e.g., between about −2 T to about 2 T) without the output saturating. In some implementations, the Hall effect sensor is used to detect a target analyte to which one or more magnetic particles have been specifically bound. Due to the linearity of the Hall effect sensor output with respect to a detected magnetic field, one can differentiate between target analytes that contain non-specifically bound magnetic particles or unbound magnetic particles by excluding measured signals from the Hall effect sensor that are below a specified threshold. Additionally, the Hall effect sensor enables detection of target analytes in a sample fluid without requiring extensive sample preparation steps.

In particular, a key challenge to implementing sensitive and practical diagnostic technology in conventional cytometers is reducing interference in the output signal from biological media (e.g., red blood cells in optical detection). The Hall effect sensors described herein, such as magnetic cytometer 100, obviate the need for processing such samples given the inherent lack of a magnetic signal in biological material. Thus, the magnetic cytometer 100 can be used as part of a point-of-care diagnostic device that enables rapid and sensitive analysis various biological fluid samples (e.g., blood, urine, sputum) for applications such as disease detection or monitoring treatment efficacy.

Figure 2:
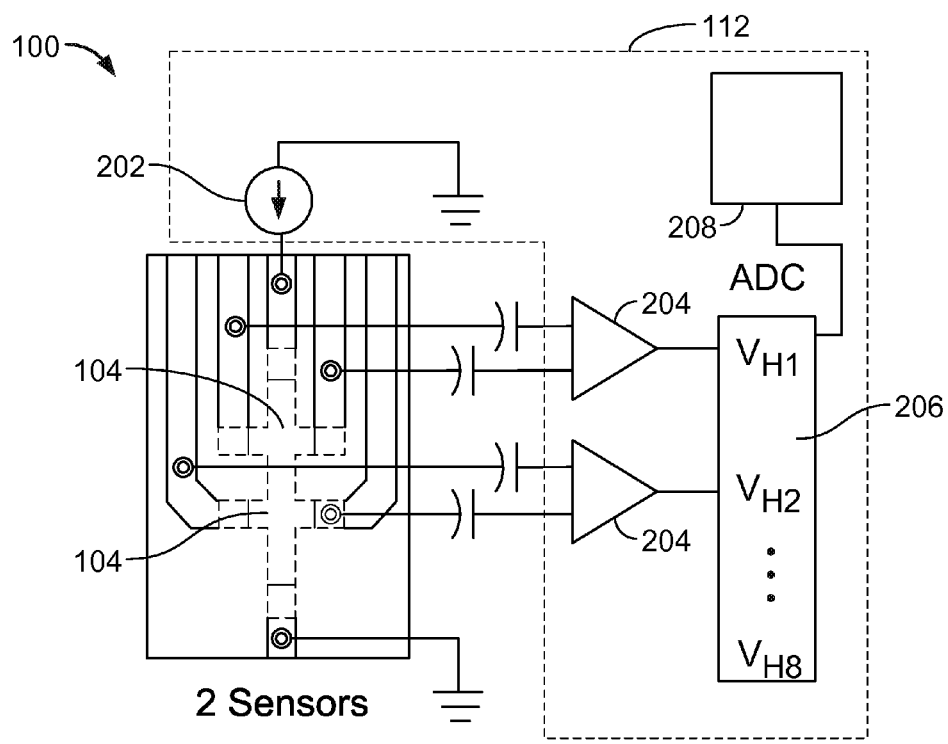
FIG. 2 is a schematic of two Hall effect sensors of a magnetic cytometer, wherein the sensors are connected in series.

FIG. 2 is a schematic of two Hall effect sensors 104 connected in series in which the outputs of the sensors are coupled to the control electronics 112 of magnetic cytometer 100. A fluidic channel positioned next to the sensors 104 typically will have a size (e.g., channel width) large enough such that a fluid flowing through the channel passes over at least the detection areas 201 of each sensor 104. The control electronics 112 include, among other things, a current source 202 to provide current to the Hall effect sensors 104, amplifiers 204, an analog-to-digital converter (ADC) 206, and electronic processor 208. During operation of the device 100, the control electronics 112 supply a current to the Hall effect sensors to generate an output voltage. When a magnetic target analyte (or analyte bound to a magnetic particle) passes a detector area of the sensors under an external magnetic field, the target analyte emanates its own magnetic field that modifies the voltage across the Hall effect sensors 104. The voltage signal from each sensor is capacitively coupled to a corresponding amplifier 204 to block the constant offset caused by the external magnetic field $B_0$. The signals are then amplified and converted into digital signals by the ADC 206. Based, on the digitized signals, the electronic processor 208 is configured to determine a position, velocity, size, and/or type of the target analyte.

Magnetic Cytometer Containing an Array of Hall Effect Sensors

Figure 3:
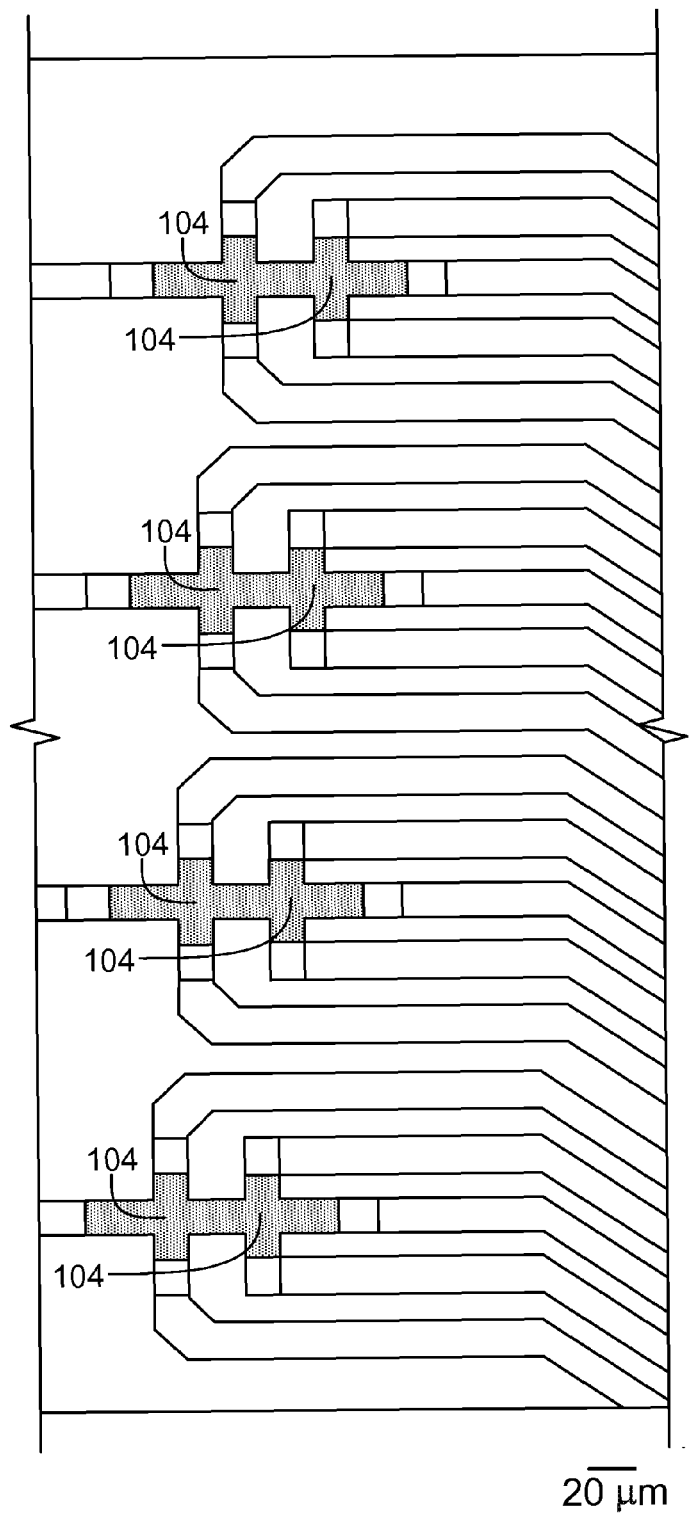
FIG. 3 is a top view of an example of a magnetic cytometer that includes eight Hall sensors arranged in a 2×4 array.

FIG. 2 shows that multiple Hall effect sensors 104 can be used in series in the magnetic cytometers described herein. In some implementations, the Hall effect sensors 104 also can be arranged in an array along a length of the fluidic channel. FIG. 3 is a top view of an example of a magnetic cytometer that includes eight Hall sensors 104 arranged in a 2×4 array. That is, the cytometer includes four pairs of Hall effect sensors 104 arranged along a length of the fluidic channel, with the sensors in each pair being coupled in series. By arranging the Hall sensors in an array, the magnetic cytometer can improve the chances of a target analyte being detected as the sample fluid passes by the sensors. For example, if the sensors 104 are each designed to have a size approximately equal to the target analyte of interest (e.g., about 8×8 μm$^2$ for a typical cell), individual analytes may pass directly over at least two Hall effect sensing elements during their passage through the microfluidic channels of the device. In addition, if the positions of the sensors are known, the location of a target analyte can, in some cases, be tracked as the analyte moves along the microfluidic channel. For example, control electronics can be configured to track a target analyte's movement based on an increase in output voltage at each Hall sensor in the device. Although FIG. 3 shows a 2×4 array of Hall sensors, the sensors can be arranged in any suitable M×N array (e.g., where M=1, 2, 4, or 6 and N=1, 2, 4, 8, 16, or 32). In some implementations, the cytometer 100 can be fabricated to include over 15, 25, 50, 75, 100, 250, 500, 750, or even a 1000 or more Hall effect sensors arranged in one or more arrays.

The Hall effect sensors can be arranged in various different patterns including, for example, a 2D rectangular lattice (e.g., similar to the arrangement of pixels in a digital camera). Arrangement of the sensors in a rectangular lattice can, in some implementations, reduce requirements for stringent fluidic control by allowing cells to spread over the device surface for measurements. Alternatively, or in addition, the sensors can be arranged along pre-determined pathways that follow the layout and direction of corresponding fluidic channels.

Magnetic Cytometer for High Throughput Analysis

Figure 4A:
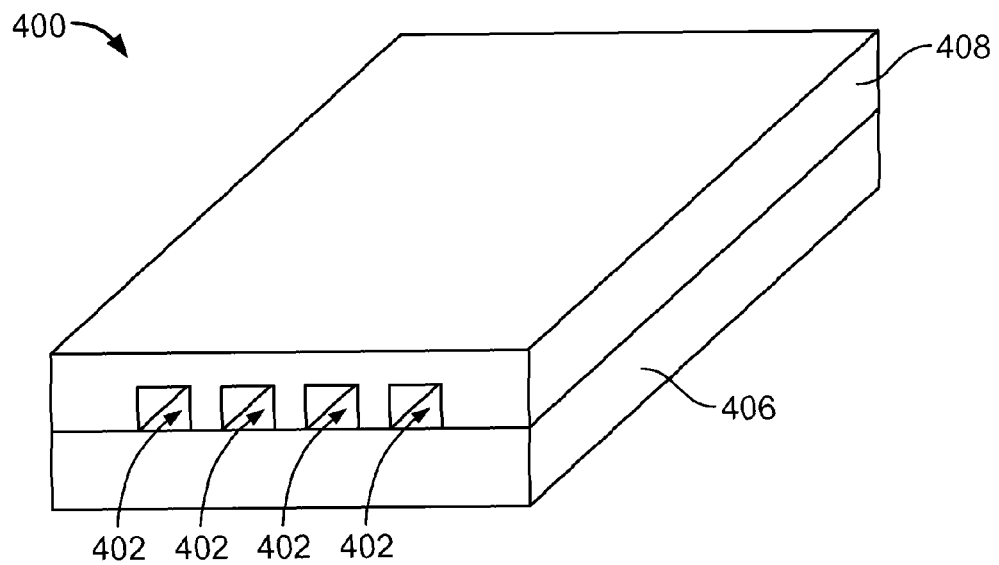
FIG. 4A is a schematic of an example of a magnetic cytometer that includes multiple fluidic channels.
Figure 4B:
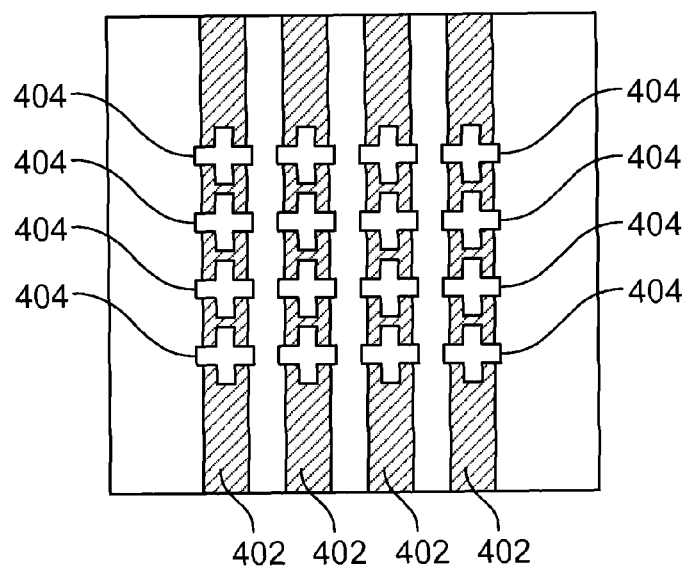
FIG. 4B is a top view of an example magnetic cytometer substrate including multiple Hall effect sensors.

In some implementations, the Hall effect sensing device can be configured to enable high throughput analysis of a fluid sample. FIG. 4A is a schematic of an example of a magnetic cytometer 400 that includes multiple fluidic channels 402 arranged in parallel on a substrate 406. The size and shape of the fluidic channels are defined by an encapsulating material 408 such as, but not limited to, polydimethylsiloxane (PDMS), glass, ceramics, plastic or epoxy photoresist. FIG. 4B is a top view of the substrate 406 including the Hall effect sensors 404. Each fluidic, e.g., microfluidic, channel 402 is aligned with one or more of the Hall effect sensors 404 on the substrate 406. By adding more fluidic channels through which the fluid sample can pass, the total volume of fluid that can be analyzed in a fixed amount of time can be substantially increased. Multiple different numbers of fluidic channels can be employed in the magnetic cytometer 400 including, for example, 2, 4, 8, 16, 32, 64, 100, 250, or 500 or more fluidic channels.

During operation of the cytometer 400, a fluid sample containing a target analyte can be delivered from a source region into the multiple fluidic channels 402, in which the target analyte includes a magnetic particle or a non-magnetic particle to which other magnetic particles are attached. A bulk magnet 408 positioned beneath the substrate 406 establishes a magnetic field $B_0$ that extends through the channels 402. The Hall effect sensors 404 in each channel detect the magnetic field emanating from the target analytes in the fluid sample as they pass through the channel over the sensors.

Whether the Hall effect sensing device includes multiple fluidic channels or a single fluidic channel, each channel can have, for example, a width of about 1, 2, 4, 8, 12 or 20 µm, a length of about 0.5, 1, 2, 4, 6, or 8 cm, and a height of about 1, 2, 4, 8, 16 or 50 µm. Other dimensions for the fluidic channels are also possible, typically depending in part on the size of the target analyte.

Magnetic Cytometers with Flow Focusing Structures

Figure 5:
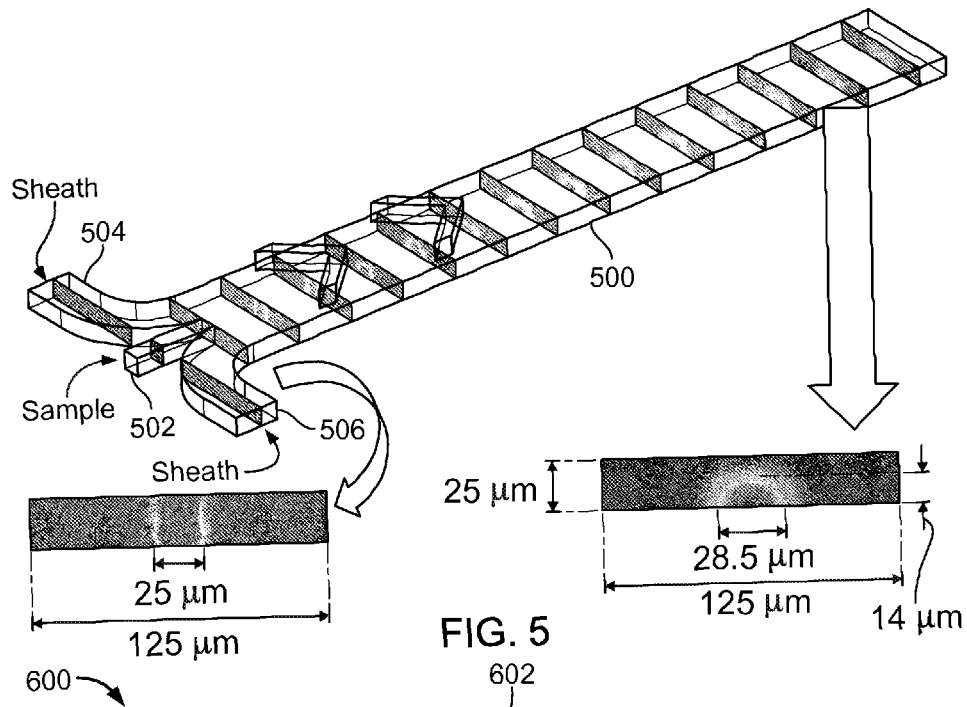
FIG. 5 is a computer simulation model of an example of a fluidic channel that produces a sheath flow

To maximize the Hall effect signal produced by the Hall sensors while minimizing variations in the output signal, the fluidic channels can be designed to include flow focusing structures that steer or confine the motion of target analytes in a fluid sample both in the lateral and vertical directions. For example, in some implementations, the cytometers can be configured to produce a sheath flow that directs target analytes in a fluid sample toward a center of the fluidic channel. FIG. 5 is a discrete element hydrodynamic computer simulation for an example of a fluidic channel 500 that produces a sheath flow. The fluidic channel 500 includes a first inlet port 502 for receiving the fluid sample, as well as a second inlet port 504 and a third inlet port 506 for receiving a sheath flow fluid. The fluid used to produce the sheath flow can be different from or the same as the sample fluid, except that the fluid used for the sheath does not include target analytes or any magnetic or magnetically labeled particles. Further information on creating sheath flow in microfluidic devices can be found, for example, in Howell, P. B. et al., "Two simple and rugged designs for creating microfluidic sheath flow," Lab Chip 8, 1097-1103 (2008).

In some implementations, the fluidic channels of the cytometers can include other flow focusing structures, such as sheathless structures formed on a top surface of the fluidic channel. Sheathless particle focusers typically rely on a force to manipulate the suspended particles to equilibrium positions. This force can be either externally applied such as acoustic, dielectrophoretic, magnetic, and optical forces, or internally induced by channel topology including hydrophoretic, inertial, and dielectrophoretic forces, among others. Therefore, the sheathless particle focusing approaches may be further classified as active or passive by the nature of the forces involved.

An example of passive particle focusing is hydrophoresis, which is the movement of suspended particles in response to a microstructure-induced pressure field. For example, the flow focusing structures can include, but is not limited to, chevron shaped patterns formed in the top walls of the fluidic channels that are arranged and configured to cause the analytes in a sample fluid to move downwards, towards the sensors, as the analytes move through the microfluidic channel or channels. Examples of chevron patterns 508 are shown in the numerical simulation model of FIG. 5. The cross-sectional images in FIG. 5 show that a sample provided through the first inlet port 502 is laterally focused toward a center of the channel 500 by the sheath flow created from fluid flowing into the channel 500 from the second inlet port 504 and third inlet port 506.

Figure 6:
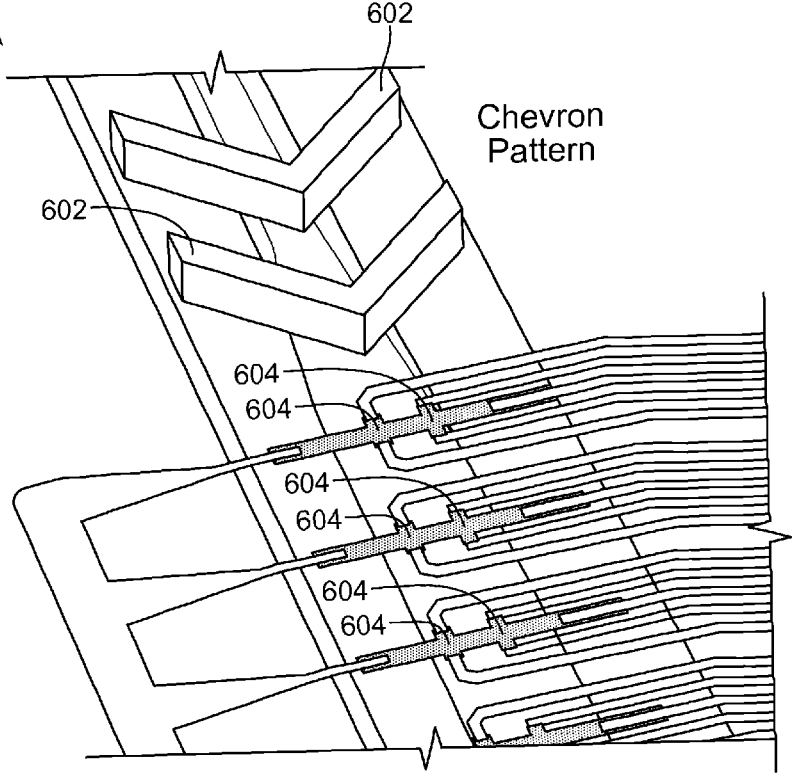
FIG. 6 is a schematic of an example of a magnetic cytometer that includes chevron patterns arranged along a top surface of a fluidic channel.

FIG. 6 is a schematic of an example of a magnetic cytometer 600 that includes chevron patterns 602 arranged along a top surface of a fluidic channel. The presence of the chevron patterns at the top of the fluidic channel serve to force target analytes in the fluid sample towards the bottom of the fluidic channel, and thus closer to the Hall effect sensors 604. Hydrodynamic flow focusing structures can, in some implementations, enable the use of microfluidic channels that are significantly larger in size relative to the targets passing through the channel. Accordingly, the risk of fluidic channel clogging can be reduced and thereby increase the robustness of the device. In addition, the pressure source for providing the fluid flow does not need to be stable, because the flow focusing is sensitive only to the relative velocities between the sheath and sample flow. Other types of applicable flow focusing structures can be found in Xuan, X., Zhu, J., Church. C., "Particle focusing in microfluidic devices," Microfluid Nanofluid, Volume 9, Number 1, 1-16 (2010).

Magnetic Cytometer Fabrication and Configuration

Figure 7:
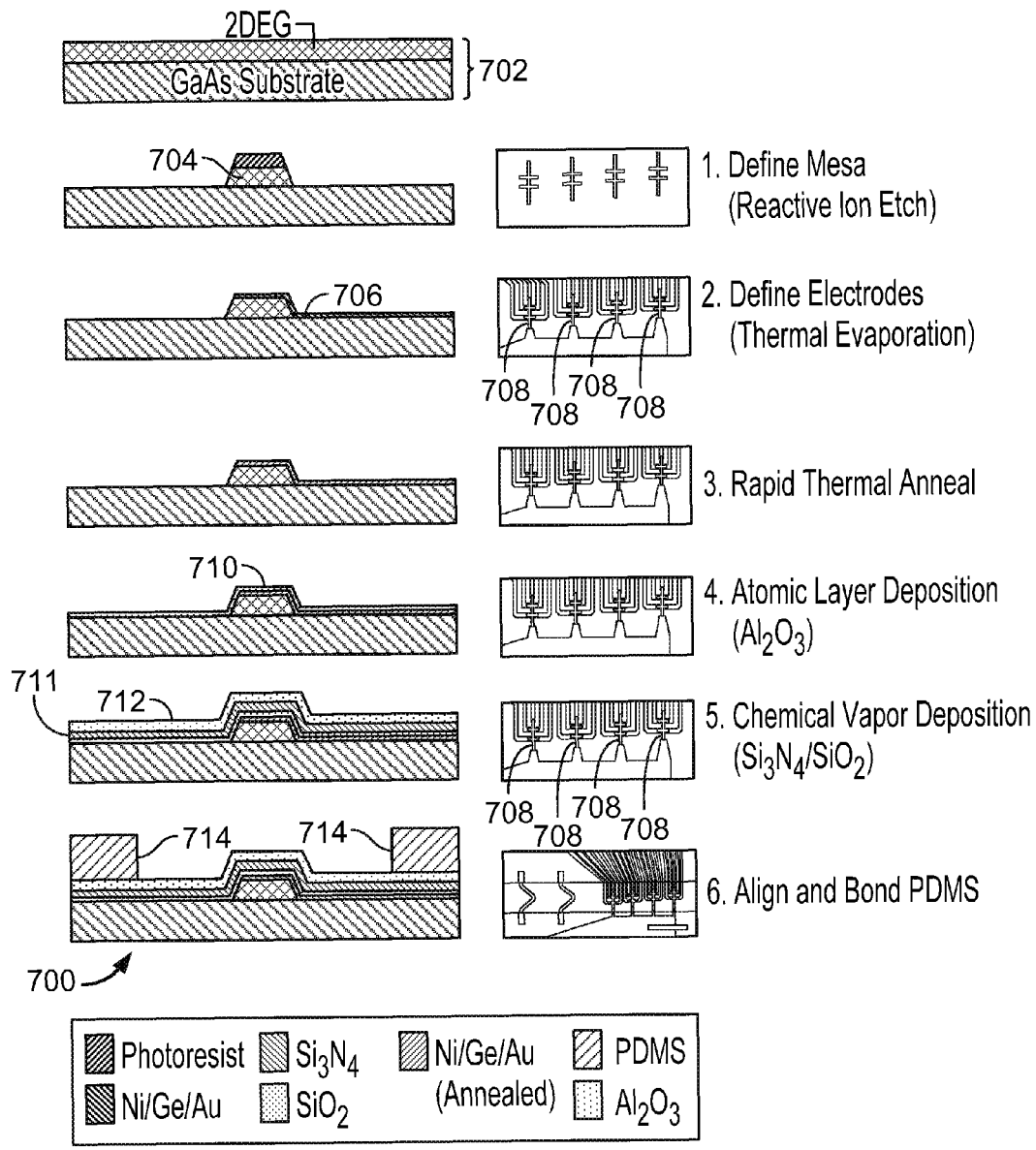
FIG. 7 is a flow diagram of one method of fabrication of a magnetic cytometer as described herein.

FIG. 7 is a flow diagram of fabrication of a magnetic cytometer 700 that includes microfabricated Hall effect sensors and a microfluidic network positioned above the sensors. The Hall effect sensors of the cytometer 700 can be constructed using metal (e.g., Au or Ag), semiconductor (e.g., indium antimonide or silicon), or devices such as high electron mobility transistor (HEMT) heterostructures (e.g., pseudomorphic HEMT heterostructures). In the example shown in FIG. 7, the Hall effect sensor is constructed using a pseudomorphic HEMT heterostructure. In short, the pseudomorphic HEMT heterostructure creates a thin low resistivity region called a two-dimensional electron gas (2DEG) between two materials having dissimilar bandgaps, in which electrons can move quickly (high mobility) without colliding with any impurities. Due to the low HEMT carrier concentration (e.g., in certain implementations the carrier concentration is about $2\times10^{12}/cm^2$), the output signal of the Hall effect sensor, which is inversely proportional to carrier concentration, can be enhanced (further information on Hall effect sensors based on pseudomorphic HEMT heterostructures can be found in, e.g., Popović, R. S., Hall effect devices. Institute of Physics, London, England (2004), pages 236-314). In general, the higher the carrier mobility and the lower the carrier concentration of the material used in the Hall effect sensor, the greater the signal to noise ratio will be in the sensor.

In a first fabrication step (701), a mesa 704 is etched from a high-electron mobility semiconductor 702, e.g., a pseudomorphic HEMT heterostructure. The high mobility semiconductor 702 can be formed using a thin layer of a first semiconductor material, e.g., AlGaAs, epitaxially deposited (e.g., using molecular beam epitaxy) on a substrate composed of a second semiconductor material, such as a GaAs substrate. The mesa can be defined using photolithography or imprint lithography followed by an etching step. e.g., an anisotropic reactive ion etch.

In a second step (703), a metal layer then is deposited on a surface of the heterostructure 702 that includes the mesa and is patterned, e.g., using photolithography and etching techniques to define electrodes 706. Patterning includes removing the metal layer in a small region 708 in the center of each Hall sensor. This region 708 corresponds to the detection area of the Hall sensor. The metal layer can include various different metals that form the electrodes. For example, the metal layer can include metals deposited in the following order and thickness: Ni (50 Å), Au (50 Å), Ge (250 Å), Au (400 Å), Ni (100 Å), and Au (400 Å). To make ohmic contact to substrate electrons by forming a eutectic alloy, the electrodes are subsequently annealed (step 705). For example, the device can be heated at a temperature between about 400° C. and 600° C. (e.g., about 430° C., 450° C., 480□C, □500□C□or□530□C) for a time sufficient to form Ohmic contacts between the electrodes and the Hall effect sensors (e.g., about 1, 2, 3, 4, 5 or more minutes using a rapid thermal annealer).

To protect the Hall sensors from biological solutions that may be used in the fluidic channels, one or more insulating layers are deposited (707) on the surface of the HEMT heterostructure and electrodes, each layer having a specific purpose. For example, a first insulating layer 710, e.g., $Al_2O_3$, can be deposited using atomic layer deposition (ALD) to about 20, 30, or 40 nm to ensure conformal coverage. A second insulating layer 711, e.g., $Si_3N_4$, can be deposited using chemical vapor deposition (CVD) to a thickness of about 50 to 200 nm, e.g., 50, 75, 100, 125, or 150 nm to protect against the diffusion of ions. A third insulating layer 712 of, e.g., $SiO_2$, can be deposited using CVD to a thickness of about 100 nm to form a layer that can be activated to permanently bond with the material used to define the fluidic channels (e.g., PDMS).

Subsequently, the microfluidic channels are fabricated and bonded (709) to the exposed surface of the oxide layer(s). In some implementations, the fluidic channels are formed by depositing a polymer (e.g., PDMS, polymethylmethacrylate (PMMA), or polycarbonate (PC)) in a mold that defines the fluidic channel regions, and then transferring the polymer to the surface of the substrate once the polymer has been cured. For example, PDMS can be first poured into a mold (e.g., an SU-8 mold fabricated with two step photolithography (MicroChem)) that defines the microfluidic network of channels. The PDMS then is cured (e.g., heating at 65° C. for about 3 hours). Prior to transferring the solid PDMS structure 710 to the device, the surface of the oxide layers is treated with $O_2$ plasma to enhance bonding.

Although the PDMS structure 710 is shown in FIG. 7 as having an open top surface, the fluidic channels can include a closed top surface such that the fluid can be confined in both the lateral and vertical directions. In some implementations, this confinement can aid in maximizing the output signal from the Hall effect sensors. In addition, the microfluidic structure 710 can be formed to include flow-focusing structures such as multiple input ports for establishing sheath flow or chevron patterns to force target analytes in fluid samples toward the Hall effect sensors.

In some implementations, the fluidic channels are configured and arranged to manipulate (e.g., merge, mix, split, heat, and/or cool, among other operations) a fluid sample. For example, the fluidic channel can be a part of a microfluidic network as described in paragraphs eighty-one to eighty-eight of U.S. Patent App. Publication No. 2011/0091987, which is incorporated herein by reference in its entirety. Microfluidic systems can be used in the magnetic cytometer 700 to facilitate control and manipulation (e.g., separation or segregation) of small volumes of liquid and help isolate targets from a complex parent specimen. During the sensing process, microfluidic elements provide functions that include, for example, handling of biological fluids, reproducible mixing of magnetic particles with samples, and distribution of aliquots to different fluidic channels for parallel sensing.

The geometry of the sensors can be optimized to achieve a high signal-to-noise ratio (SNR) for cellular detection. In some implementations, the SNR can be maximized when the Hall effect sensors have a size similar to the target analyte being measured. For example, for detection of mammalian cells, the detection region 708 of each Hall effect sensor can be designed to have an area of about $8\times8$ m$^2$. Other sizes for the detection region 708 also are possible including, for example, an area of about $1\times1$ μm$^2$, $2\times2$ μm$^2$, $4\times4$ m$^2$, $5\times5$ μm$^2$, $12\times12$ μm$^2$, or $16\times16$ μm$^2$. The detection region 708 for each Hall effect sensor does not have to be symmetric and instead can include, for example, sides of varying length. For the detection of bacterial cells, the sensor size can be, e.g., $2\times2$ μm or $250\times250$ μm$^2$.

Figure 13B:
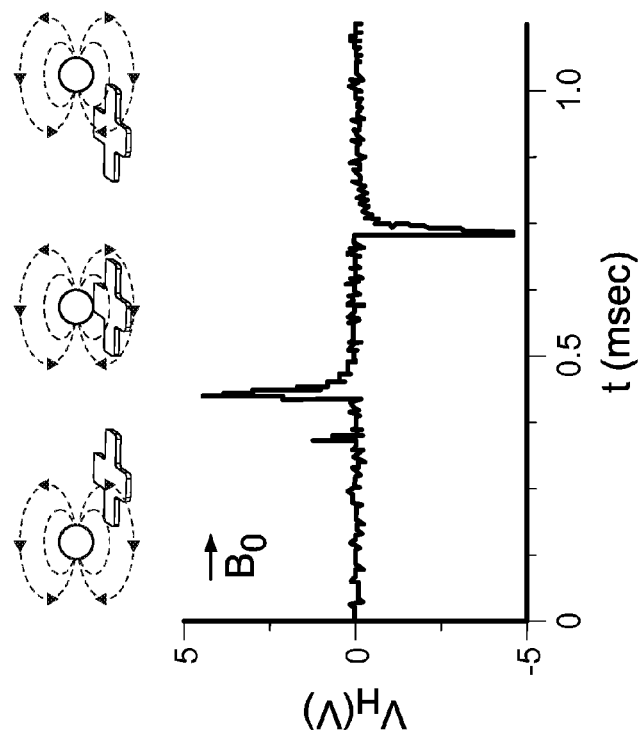
FIG. 13B is a plot showing a measured Hall signal from the passing of a single magnetic bead for an external magnetic field applied in the plane of the magnetic cytometer.

Once the device 700 is constructed, the external magnetic field can be provided using a small permanent magnet (e.g., approximately 1 cm) positioned directly beneath the chip. The permanent magnet can be any suitable permanent magnet (e.g., NdFeB or SmCo) for providing a static polarizing magnetic field (e.g., about 0.001 T, 0.1 T, 0.3 T, 0.5 T, 1.5 T, or 2 T). The magnetic field can be oriented such that it is parallel to the plane that includes the Hall effect sensor surface facing the fluidic channel (e.g., the top surface of the Hall effect sensor) or perpendicular to the surface of the Hall effect sensor that faces the fluidic channel. Orienting the magnetic field perpendicular to the Hall effect sensor surface induces larger output voltages than orienting the field to be parallel to the sensor surface. Orienting the magnetic field parallel to the plane of the sensor surface leads to a measurement of two separate peaks by the Hall effect sensor, in which the peaks have opposite polarity (see, e.g., FIG. 13B). The out-of-plane mode therefore is, in some implementations, better suited for studies in which an accurate measurement of the magnetization of a passing analyte is important. In contrast, the in-plane mode is better suited to count target analytes having a low concentration in the sample fluid being passed over the Hall effect sensor(s) because it allows one to screen for the distinct bipolar response of the voltage sensor as a magnetic particle passes by, thus reducing the probability of a false-positive detection occurring.

Sample Preparation

The fluid sample to be used in the Hall effect sensing device can include, for example, turbid samples such as blood, sputum, urine, or samples that have been prepared using techniques including, but not limited to, filtering or centrifugation. As noted above, a target analyte in the fluid sample can be mixed with a number of magnetic particles (e.g., nanoparticles) that are designed to specifically bind to the target analyte to form a target-particle complex in solution. Alternatively, or in addition, a collection of target analyte-particle complexes are stuck/joined/bound together to form a "cluster" of complexes. For example, each magnetic particle can include two or more binding moieties, so that each magnetic particle can bind to at least two target analytes, and each analyte can be bound to multiple magnetic particles as well.

Magnetic particles include one or more inner magnetic cores and an outer coating, e.g., a capping polymer. The magnetic cores can be monometallic (e.g., Fe, Ni, or Co), bimetallic (e.g., FePt, SmCo, FePd, or FeAu) or can be made of ferrites (e.g., $Fe_2O_3$, $Fe_3O_4$, $MnFe_2O_4$, $NiFe_2O_4$, or $CoFe_2O_4$). The magnetic particles can be nanometers or micrometers in size, and can be diamagnetic, ferromagnetic, or superparamagnetic. The outer coating of a particle increases its water-solubility and stability and also provides sites for further surface treatment to attach or link binding moieties.

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as specific enzymes in solution. Such substrates may then be cleaved by the enzymes in a sample that are specific for that substrate in a manner that can be detected using the new systems and methods.

Binding moieties include, for example, oligonucleotide binding moieties, polypeptide binding moieties, antibody binding moieties, and polysaccharide binding moieties. As an example, streptavidin has four sites (binding moieties) per molecule that will be recognized by biotin. In general, antibodies are selected to specifically bind to specific cell surface markers, and different types of cells, e.g., white blood cells, circulating tumor cells, fetal cells in maternal blood, and bacterial cells. Each cell type has different and unique surface markers. Accordingly, antibodies are selected to specifically bind to the surface markers that are unique for the desired target analyte. The antibodies can include, but are not limited to, anti-EpCAM, anti-HER2, and anti-epithelial growth factor receptor (EGFR).

The surface of the magnetic particles are treated to present functional groups (e.g., $-NH_2$, $-COOH$, $-HS$, $-C_nH_{2n-2}$) that can be used as linkers to subsequent attachments of other molecules (e.g., antibodies, drugs). In some cases, the surface treatment makes the magnetic particle essentially hydrophilic or hydrophobic. The surface treatment can be formed of polymers including, but not limited to, synthetic polymers such as polyethylene glycol or silane, natural polymers, derivatives of either synthetic or natural polymers, and combinations thereof.

In some implementations, the surface treatment is not a continuous film around the magnetic particle, but is a "shell," "mesh" or "cloud" of extended polymer chains attached to and surrounding the magnetic particle. Exemplary polymers include, but are not limited to, polysaccharides and derivatives, such as dextran, pullanan, carboxydextran, carboxmethyl dextran, and/or reduced carboxymethyl dextran, polymethylmethacrylate polymers, and polyvinyl alcohol polymers. In some implementations, these polymer coatings provide a surface to which targeting moieties and/or binding groups can bind much easier than to the shell material. For example, in some embodiments magnetic particles (e.g., iron oxide nanoparticles) are covered with a layer of 10 kDa dextran and then cross-linked with epichlorohydrin to stabilize the coating and form cross-linked iron oxide (CLIO) magnetic particles. (Additional information on the fabrication, modification and use of magnetic particles can be found, for example, in PCT Pub. No. WO/2000/061191, U.S. Patent App. Pub. No. 20030124194, U.S. Patent App. Pub. No. 20030092029, U.S. Patent App. Pub. No. 20060269965, Hogemann, D., et al., "Improvement of MRI probes to allow efficient detection of gene expression," Bioconjug. Chem. 2000. 11(6):941-6, Josephson et al., "High-efficiency intracellular magnetic labeling with novel superparamagnetic-Tat peptide conjugates," Bioconjug. Chem., 1999, 10(2): 186-91, Shen et al., "Magnetically labeled secretin retains receptor affinity to pancreas acinar cells," Bioconjug. Chem., 1996, 7(3):311-6)).

Applications

The new Hall effect sensing device devices described herein can be used in a variety of applications for detecting and/or profiling any micrometer-scale objects, including micro-scale magnetic objects. These applications include diagnostic testing near a patient (so called "point-of-care" testing). For example, the Hall effect sensing devices can be incorporated into portable electronic devices and systems and can be used in resource-limited and/or remote settings including, for example, in an ambulance, in an emergency room, in an intensive care unit, or in other patient settings for the rapid, quantitative, and multi-channeled detection of biological targets. Furthermore, the new systems can simplify use and data logging/sharing for medical personal through a mobile computing device interface. Examples of detection uses and targets are discussed in more detail below and in the Examples section.

Other applications for the new Hall effect sensing devices include environmental and agricultural monitoring of chemical or biological analytes such as pathogens, toxins, and pollutants for damage to livestock or the environment and for defense purposes. In addition, the Hall effect sensing devices can be used to monitor target analytes in industrial settings (e.g., to determine the presence of unwanted particles that could disrupt industrial processes or contaminate food or beverages).

Determining Position, Velocity, Size, and Type of Target Analyte

Figure 13A:
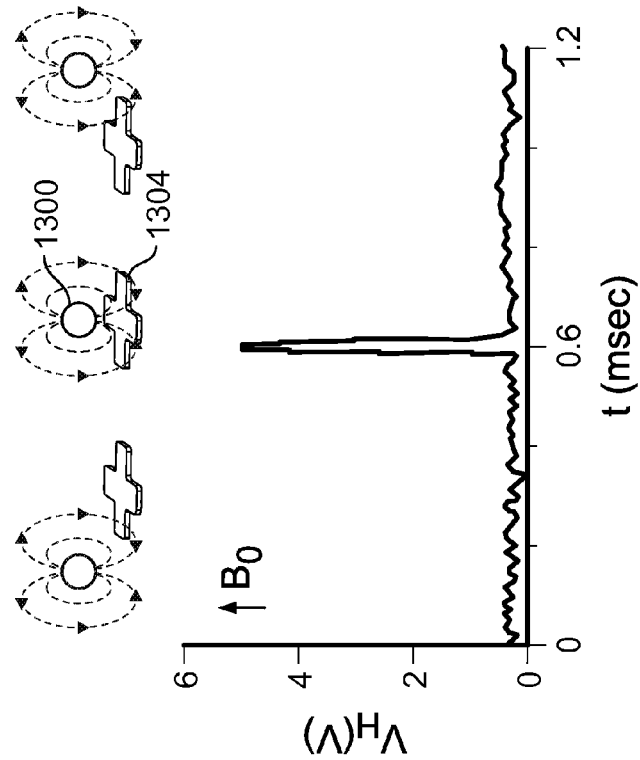
FIG. 13A is a plot showing a measured Hall signal from the passing of a single magnetic bead for an external magnetic field applied out of the plane of the magnetic cytometer.

As explained herein, the control electronics for the Hall effect sensing device can be configured to determine, for example, the presence, position, velocity, size, and/or type of the target analyte in the fluid sample. For example, the control electronics can be configured to identify the presence of a target analyte if the measured output voltage signal from a Hall effect sensor rises above a specified threshold value as the target analyte passes over a detection region of the sensor. FIG. 13A is a plot of an example of a time domain measurement of a single magnetic bead 1300 passing over a Hall effect sensor 1304. As illustrated in the plot, the output voltage $V_H$ from the Hall effect sensor spikes as the magnetic bead 1300 passes over a detection region of the sensor 1304, indicating the presence of the bead 1300. The duration of the output signal spike shown in FIG. 13A is proportional to the time the magnetic bead 1300 is over the detection region of the Hall effect sensor 1304. Thus, if the interaction length of the sensor is known, a velocity of the target analyte can be estimated.

When an array of Hall effect sensors is employed in the Hall effect sensing device, the effective sensing area is increased, such that a substantial portion of the magnetic flux from the magnetic dipole can be can be detected. Accordingly, in some implementations, the total magnetic flux from a target analyte in the sample fluid can be estimated. For example, FIGS. 8 and 9 are schematics of a target analyte 900 located above the effective sensing area of a Hall effect sensor. As shown in FIG. 8, the effective sensing area 902 is about 64 μm$^2$ whereas the effective sensing area 904 in FIG. 9 is about 512 μm$^2$. Accordingly, the sensing area shown in FIG. 9 senses a greater amount of flux (indicated by more dashed lines crossing the sensor array as they emanate from analyte 900) from the target particle than the sensing area of FIG. 8.

For the first approximation, the expected dependence of the output signal $V_H$ on the sensor area can be estimated as follows. Referring to FIG. 10A, when a magnetic object 1000 is located at a distance d above a Hall effect sensor 1004, the solid angle Ω from the object to the sensor can be expressed as:

$$\Omega \approx 2\pi \cdot (1 - \cos\theta) = 2\pi \cdot \left(1 - \frac{d}{\sqrt{d^2 + (L/2)^2}}\right)$$

where L is the lateral dimension of the Hall sensor. The total flux then can be estimated as $\varphi \approx \Omega \cdot d^2 \cdot B_\perp$, where $B_\perp$ is the magnetic field strength ($\sim d^{-3}$) at the sensor surface. Depending on the size of the sensor (e.g., a single element vs. array), 4 can be approximated as shown in the following Table 1.

TABLE 1

| Single Hall element | Array of Hall sensors |
|---|---|
| $d \gg L$ | $d \ll L$ |
| $\Omega \approx \pi \cdot \left(\frac{L}{2d}\right)^2$ | $\Omega \approx 2\pi \cdot \left(1 - \frac{2d}{L}\right)$ |
| $\Phi \propto \pi \cdot \left(\frac{L}{2d}\right)^2 \cdot d^2 \cdot \frac{1}{d^3} \propto \frac{L^2}{d^3}$ | $\Phi \propto 2\pi \cdot \left(1 - \frac{2d}{L}\right) \cdot d^2 \cdot \frac{1}{d^3} \propto \frac{1}{d} - \frac{2}{L}$ |

Figure 10C:
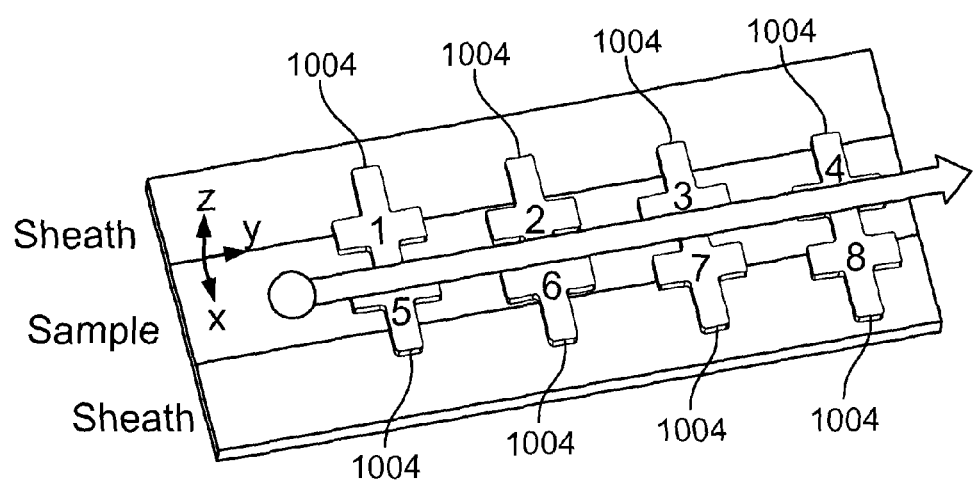
FIG. 10C is a schematic of an example of multiple Hall effect sensors arranged in a 2×4 array.

Therefore, by effectively increasing the sensor area using the array format and capturing more magnetic flux from the dipole, the total flux is less dependent on the distance between the particle and the sensor ($d^{-1}$ rather than $d^{-3}$). FIG. 10C is a schematic of multiple Hall effect sensors 1004 (numbered 1-8) arranged in a 2×4 array, in which the pairs of the array are laterally staggered across the width of the channel. FIG. 10B is a plot of an example of a simulation of the Hall sensor output voltage versus vertical distance from the effective sensing area of the multiple Hall sensors 1004 shown in FIG. 10C. The output voltage corresponds to an average output voltage of the sensors in the array. As shown in FIG. 10B, over the range of 0-10 μm above the sensor's surface, there is less than a 15% shift in the Hall voltage VH. Thus, the sensor array is effectively insensitive to variations in the vertical position of a target analyte above the sensor's detection region, leading to a more robust and reliable detection technique that ensures detection of most if not all target analytes passing through a fluidic channel.

Figure 10D:
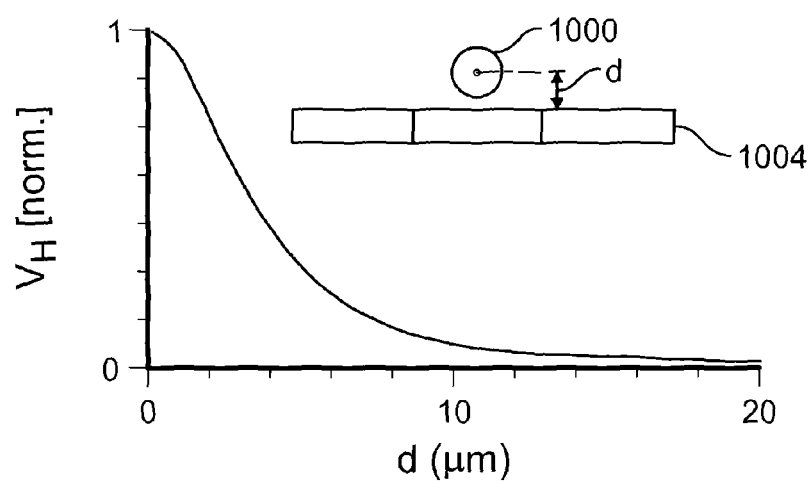
FIG. 10D is a plot of a simulation of a Hall effect sensor output voltage versus vertical distance from the single Hall effect sensor.

FIG. 10D is a plot of an example of a simulation of the Hall sensor output voltage versus vertical distance from a single Hall effect sensor 1004. In contrast to the average voltage output shown in FIG. 10B, the change in voltage for a single hall sensor as the vertical position of the target analyte changes is about 80%. Accordingly, if a single Hall sensor is used, and the height of the fluidic channel is known, the control electronics in the Hall effect sensing device can be configured to determine a vertical position of the analyte in the fluidic channel.

Figure 10E:
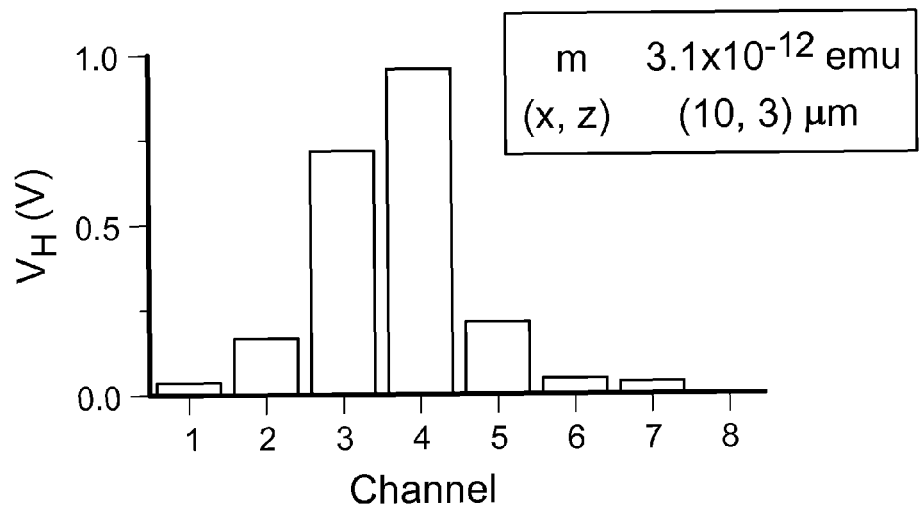
FIG. 10E is a plot of simulated output voltage for each of the eight Hall effect sensors of FIG. 10C.

The output of the Hall sensor also is highly susceptible to variations in the lateral position of the magnetic dipole associated with the target analyte. FIG. 10E is a plot of simulated output voltages (numbered 1-8) for each of the eight Hall effect sensors 1004 of FIG. 10C as a target analyte passes through a fluidic channel and over the sensing areas of each sensor. The position of the target analyte is fixed in the lateral and vertical directions. The x and z coordinates shown in the graph are measured from the origin, which is shown in FIG. 10C as the intersection of the x, y and z-axes. The magnitude of the output voltage recorded by each sensor 1004 is proportional to the extent the target analyte travels over a detection region associated with the sensor. Accordingly, when the particle is confined in the vertical direction (e.g., using flow control structures or channel heights slightly larger than the target analyte size), the voltage information from a Hall sensor array can be used to determine a lateral position of the target particle as it passes through a fluidic channel.

Figure 11:
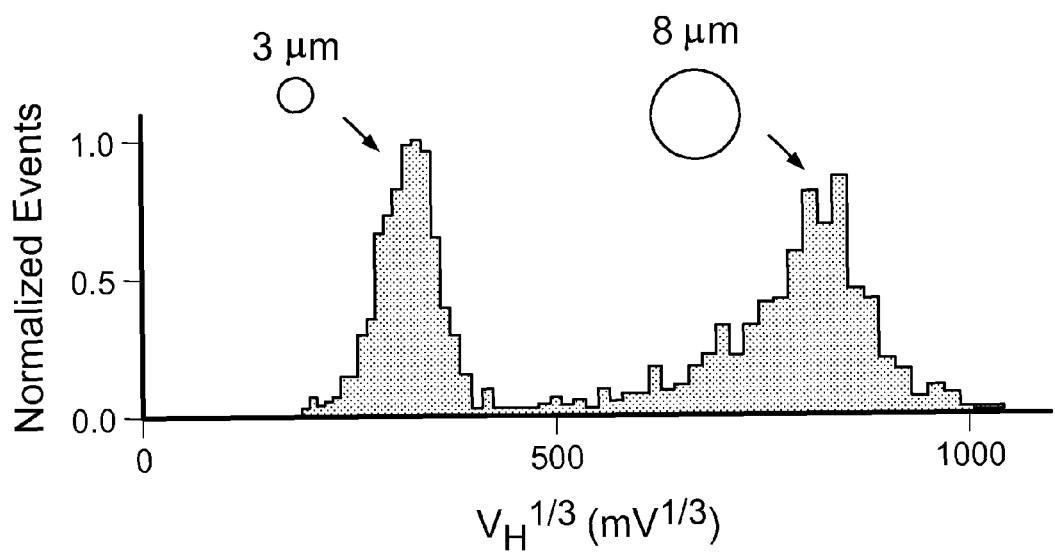
FIG. 11 is a histogram plot of the average voltage recorded by the Hall effect sensor array in FIG. 10C for magnetic beads 3 μm in diameter and 8 μm in diameter.

The output voltage of a Hall sensor also can serve as an effective metric for comparing different sized target analytes or the relative number of magnetic particles bound to a target analyte. For example, magnetic particles composed of the same material, but having a different size, will produce magnetic fields with magnitudes that are proportional the particle size. Similarly, in some implementations, target analytes may bind to more or fewer magnetic particles in proportion to the particle volume, thus leading to a proportional variation in magnetic moment. In other implementations, the number of magnetic particles bound to each analyte depends on the density of surface markers on the analyte to which the binding moieties bind. FIG. 11 is a histogram plot of the average voltage recorded by the sensor array in FIG. 10C for magnetic beads 3 μm in diameter and 8 μm in diameter. As shown in the plot, two distinct peaks of output voltage are visible, in which the first peak corresponds to the voltage recorded for 3 μm beads and the second peak corresponds to the voltage recorded for 8 μm beads. The ratio between the peak values is about 2.7, which is close to the expected ratio of 8/3. Thus, the new systems can be used to distinguish the size of different analytes in the same sample.

Detecting Infectious Agents and Rare Analytes

The Hall effect sensing devices described herein provide a modular platform. By modifying the binding moieties on magnetic particles, the same Hall effect sensing device can be used to measure many different target analytes, such as biological targets, including small molecules, proteins, nucleic acids, pathogens, cancer cells (such as circulating tumor cells (CTCs) that can be present in blood), and cancer cell markers. Other types of analytes include toxins in food or water samples, contaminating particles and pathogens in industrial and agricultural fluids, etc. Once the magnetic particles are configured with the appropriate binding moieties, the target analytes can be easily detected with minimal preparation steps (e.g., no need for intensive purification steps).

The new systems and methods can be used to detect rare cells in biological fluids (e.g., circulating tumor cells (CTC) in a blood sample using antibodies to the EpCAM surface protein as the binding moieties, fetal cells in maternal blood samples using antibodies to fetal cell markers such as anti-fetal hemoglobin antibody, endothelial cells using antibodies to cell surface markers such as CD146, immune cells, and stem cells). For example, primary tumor cells or circulating tumor cells can be targeted with magnetic particles and can be detected using the new Hall effect sensing device for a rapid and comprehensive profiling of cancers. By changing the binding moieties on the magnetic particle surface, different types of analytes, such as cells can be detected (e.g., circulating endothelial cells for heart disease). Thus, the Hall effect sensing device can be used as a powerful diagnostic and prognostic tool. In some implementations, the system sensitivity can detect as low as a few cells per microliter of detection volume, i.e., the device itself has the capacity for single-cell detection.

Detecting Bacteria

Another example of an infectious biological target that the Hall effect sensing device can detect is bacteria. In some implementations, the Hall effect sensing device can be configured to directly measure one or a few, magnetically tagged bacteria in clinical specimens with little sample processing. Similar to other examples described herein, target bacteria are first labeled with molecular-specific magnetic nanoparticles, e.g., antibodies to surface markers that are or can be attached to magnetic nanoparticles before or after the antibodies are bound to the surface of a bacterium. The fluid containing the tagged bacteria then is introduced into the Hall effect sensing device, where the miniaturized Hall sensors subsequently detect the tagged bacteria. Due to their small size (~1 μm), bacteria can be streamed to the sensor surface to enhance detection of individual bacteria. In addition, individual bacteria can be labeled using bio-orthogonal nanoagents to achieve efficient and maximal magnetic nanoparticle-loading on bacterial targets. A discussion of the use and operation of bio-orthogonal nanoagents can be found, for example, in Chung et. al., ACS Nano, 2011, vol. 5, p. 8834.

In some implementations, the Hall effect sensing device can differentiate between individual pathogens and unbound particles or between individual pathogens and undesired targets to which the magnetic particles bind. In particular, since pathogens can be configured to bind to a large number of magnetic particles per individual pathogen (and thus be associated with a large magnetic moment), the signal arising from unbound particles or undesired targets to which the magnetic particles bind would be negligible in comparison. Consequently, in some implementations, the negligible magnetic background produced by non-specific labeling or free magnetic particles enables highly sensitive measurements and minimizes a need to purify the sample before performing the measurement. By reducing or eliminating the number of purification steps, pathogen (e.g., bacterial) loss prior to measurement can be minimized and the assay procedure can be significantly simplified for clinical use.

Additionally, the entire measurement can be performed using a single microfluidic chip, which eliminates the need for laboratory infrastructure and trained personnel. The assay could be adapted to differentiate a variety of other bacterial species by changing the affinity ligands. With such capacities, the magnetic cytometer devices can be used as comprehensive and universal diagnostic platforms with potentially broad clinical applications in resource-limited, point-of-care settings.

Figure 19A:
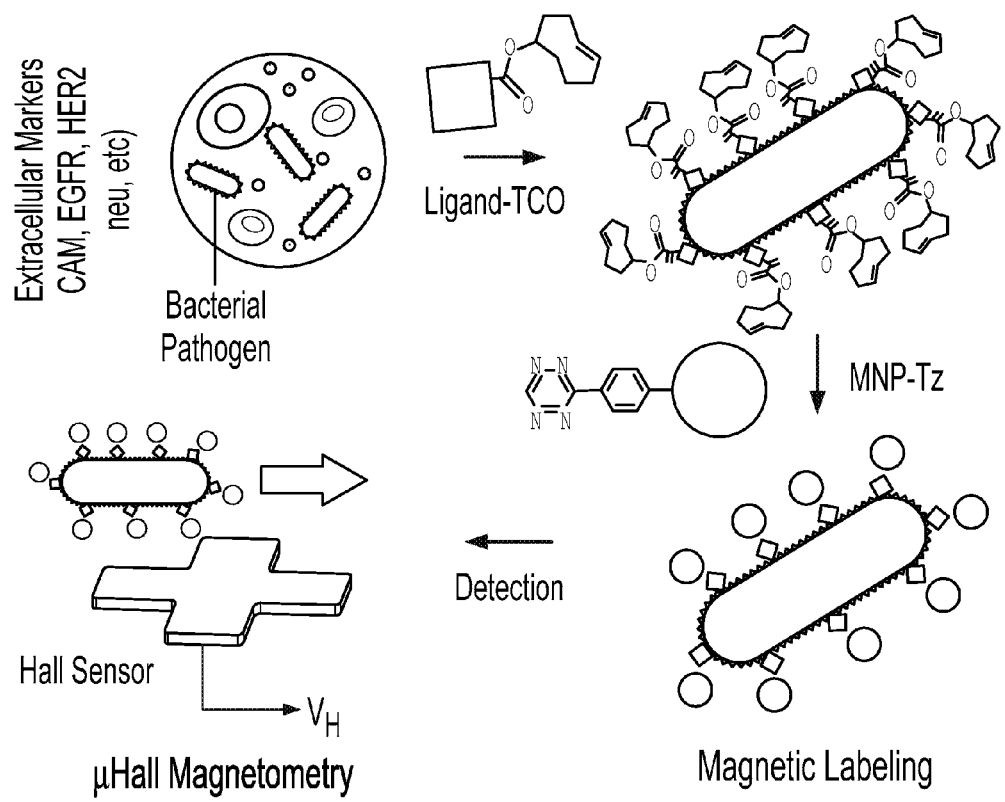
FIG. 19A is a schematic that illustrates an example of an assay scheme.

FIG. 19A illustrates an example of the assay scheme. Bacteria in solution are initially labeled with magnetic particles (e.g., magnetic nanoparticles) targeting specific molecular surface markers to render the bacteria superparamagnetic. Consequently, when subjected to external magnetic fields, each bacterium assumes a magnetic moment m, which is proportional to the number of expressed biomarkers N and the magnetic moment of the magnetic nanoparticles, $m_p$, i.e., $m=N \times m_p$. The local magnetic fields emanating from individual bacteria then can be measured by the Hall effect sensors of the Hall effect sensing device, where peaks in Hall voltage ($V_H$) occur as single bacterium flow over the sensor.

Nucleic Acid Detection

Besides its application as a cytometer, the Hall effect sensor can also be used to detect nucleic acids, including DNAs, messenger RNAs (mRNAs), and micro RNAs (miRNAs). In these types of assays, target nucleic acids are detected using a sandwich-type hybridization. The detection could be performed in two ways: cytometry format and surface immobilization.

In the cytometry format assay, the target nucleic acids are first captured by polymeric microbeads. These microbeads are preconjugated with oligonucleotides that have a complementary sequence to the target nucleic acids. Subsequently, the beads are incubated with magnetic nanoparticles that have another oligonucleotides with complementary sequences. In this way, the polymeric beads can be cover with magnetic nanoparticles. By flowing these beads over the sensors, one can eventually detect the target nucleic acids.

In the surface immobilization assay, the surface of the Hall sensing element is initially modified with captured oligonucleotides using standard techniques known in the art, in which the captured oligonucleotides have a complementary sequence to target nucleic acids. Sample fluid then is provided to the Hall effect sensor and target nucleic acids within the sample fluid are captured by the corresponding oligonucleotides bound to the Hall sensing element surface. Subsequently, another fluid containing complementary oligonucleotides conjugated with magnetic particles then is introduced into the device. The complementary oligonucleotides then bind to the previously bound target nucleic acids to complete the magnetic labeling. In contrast to the cytometry assay that detects cells in flow, the hybridized nucleic acid complexes can be detected by operating the Hall effect sensor in the direct-current (DC) mode. That is, one can simply apply external magnetic fields and read out the Hall voltages ($V_H$). The $V_H$ values will be proportional to the concentration of target nucleic acids bound to the sensor surface, thus enabling quantitative measurements of the nucleic acid strands.

Multiplexed Detection

Detecting multiple biomarkers in one parent sample is also an important and highly desirable task for diagnosis and prognosis of complex diseases. For example, it is rare that an individual cell can be identified based on the measurement of a single biomarker alone; multi-channeled screening is typically required to correctly identify tumor types.

The basis for multiplexed magnetic cytometry is similar in principal to multiplexing in flow cytometry (FCM). Rather than using different fluorescence spectra, the unique magnetization properties of magnetic particles are exploited in the present methods and systems to distinguish targeted biomarkers. Specifically, cells are labeled with different types of magnetic particles with each type targeting a different biomarker. Subsequently, the total magnetic moment m of each cell is measured by the Hall effect sensors at several different magnetization fields B, while the cell is flowing through a fluidic channel. Using the measured magnetic responses and the known magnetic properties of MNPs, the number of each MNP type per cell then can be calculated.

For example, when a cell is targeted by three different types of MNPs, with each type of MNP specific to a different biomarker, the total magnetic moment m at a given magnetic field (B) can be expressed as $$m = N_a V_a L_a(B) + N_b V_b L_b(B) + N_c V_c L_c(B), \quad (eq.\ 1)$$

where $N_i$, $V_i$, and $L_i$ represent the number, volume and magnetization of the MNP used (i=a, b, c). By measuring m at three different field strengths, one can obtain a set of linear equations $$\begin{pmatrix} m_1 \\ m_2 \\ m_3 \end{pmatrix} = \begin{pmatrix} V_a L_a(B_1) & V_b L_b(B_1) & V_c L_c(B_1) \\ V_a L_a(B_2) & V_b L_2(B_2) & V_c L_2(B_2) \\ V_a L_a(B_3) & V_b L_b(B_3) & V_c L_c(B_3) \end{pmatrix} \cdot \begin{pmatrix} N_a \\ N_b \\ N_c \end{pmatrix}, \quad (eq.\ 2)$$

which can be solved to obtain ($N_a$, $N_b$, $N_c$).

$$\begin{pmatrix} N_a \\ N_b \\ N_c \end{pmatrix} = \begin{pmatrix} V_a L_a(B_1) & V_b L_b(B_1) & V_c L_c(B_1) \\ V_a L_a(B_2) & V_b L_b(B_2) & V_c L_c(B_2) \\ V_a L_a(B_3) & V_b L_b(B_3) & V_c L_c(B_3) \end{pmatrix}^{-1} \cdot \begin{pmatrix} m_1 \\ m_2 \\ m_3 \end{pmatrix}. \quad (eq.\ 3)$$

Note that the number of biomarkers that can be measured using this technique is limited only by the accuracy of the magnetization measurement and the material properties of the MNPs.

Multiplexed detection on individual cells is made possible by the linearity of the Hall-effect sensors. The transient signal from a passing cell can be measured using AC coupled amplifiers and the applied field using DC coupled amplifiers. With this strategy, cells can be measured at a wide range of applied fields without the need for bulky and expensive electromagnets typically used to produce varying magnetic fields. Rather, inexpensive and compact permanent magnets can be used to make spatially varying fields. By placing several Hall effect sensors in the spatially varying field, high accuracy measurements of magnetic properties as a function of applied magnetic field can be acquired.

EXAMPLES

The invention is further described in the following example, which does not limit the scope of the invention described in the claims.

Example 1: Device Fabrication and System Evaluation

A magnetic cytometer was fabricated and evaluated to determine performance. To fabricate the cytometer, the fabrication steps outlined above and shown in FIG. 7 were followed. In particular, a mesa was etched out of a pseudomorphic high electron mobility transistor (PHEMT) heterostructure, in which the heterostructure included epitaxially grown AlGaAs on a GaAs substrate. The mesa was defined using photolithography followed by an anisotropic reactive ion etch. Electrodes were formed by photolithographically-patterning metal layers deposited on the substrate in the following order: Ni (50 Å), Au (50 Å), Ge (250 Å), Au (400 Å), Ni (100 Å), and Au (400 Å). The metal layers were deposited using thermal evaporation. To make ohmic contact to substrate electrons by forming an eutectic alloy, the electrodes were subsequently annealed at 480° C. for 90 seconds using a rapid thermal annealer.

The Hall sensors were protected from the biological solutions using three layers of oxide, each with a specific purpose: an atomic layer deposition (ALD) grown 30 nm $Al_2O_3$ to ensure conformal coverage, a chemical vapor deposition (CVD) grown layer of 100 nm $Si_3N_4$ to protect against the diffusion of ions, and a CVD grown layer of 100 nm $SiO_2$ to form a layer that can be activated to permanently bond with the PDMS.

The microfluidic channels were fabricated using standard soft lithography. A two layer SU-8 (MicroChem) mold was fabricated with two step photolithography. PDMS was poured onto the mold and cured at 65° C. for 3 hours. The PDMS microfluidics and GaAs chip were treated with $O_2$ plasma, aligned using a modified mask aligner, and permanently bonded. The sensors were arranged in a 2×4 array as shown in FIG. 3. Each pair of Hall effect sensors in the array was coupled in series such that current could be provided to each sensor pair from a single source.

FIG. 12A is a schematic of the control electronics 1200 used to operate the Hall effect sensors in the magnetic cytometer. The control electronics 1200 included multiple current sources 1202, in which each current source 1202 was coupled to a Hall effect sensor pair 1204. The output voltage of the Hall sensors was AC coupled to a corresponding two-stage amplifier 1206 (including a pre-amplifier and amplifier, THS4131, Texas Instruments) through a high pass filter (HPF). High speed, low input impedance, bipolar, differential amplifiers were used for both stages of amplification. These amplifiers were impedance matched to the Hall sensors, and had a bandwidth of 150 MHz. The HPF was configured to have a 3 dB frequency of about 500 Hz to filter the DC external magnetic field. The output of each amplifier 1206 was passed to ADC 1208 (PCI 6133, National Instruments). The output signal was then digitized (about $2 \times 10^6$ samples/s to about $2.5 \times 10^6$ samples/s) by the ADC 1208 and analyzed by software using electronic processor 1210. The gain of the two-stage amplifier was about 900 (i.e., a gain of 30 for each amplifier).

We first characterized the electrical properties of individual Hall sensors. The sensitivity of the microfabricated Hall sensors was evaluated by placing the sensors in a known magnetic field and measuring the corresponding output voltage (see FIG. 12B). The magnetic field was created using a water cooled electromagnet (HV-4H, Walker LDJ Scientific) and independently measured using a commercial magnetometer (THM 7025, MetroLab). The Hall resistance (RH) was measured to be 78 Ω/T. The noise within the chip's bandwidth (1 kHz-2 MHz) was measured using a spectrum analyzer and determined to be about 1.3 nV/Hz1/2 (see FIG. 12C). From the typical driving current (2 mA) and the target SNR (about 10) for reliable detection, the minimum magnetic field detectable was about 40 μT.

The magnetic particles used to evaluate the cytometer were cross-linked iron oxide (CLIO) particles. These CLIO nanoparticles have a core size of 7 nm and a hydrodynamic diameter of 30 nm. Given the magnetic moment of the iron oxide nanoparticles ($3 \times 10^{-17}$ emu), the minimum number of particles that could be detected was calculated to be about 2000. The detection sensitivity can be further enhanced (>50 times) by using magnetic nanoparticles with higher magnetic moments (see, e.g., Lee, H., Yoon, T. J. & Weissleder, R., "Ultrasensitive detection of bacteria using core-shell nanoparticles and an NMR-filter system," Angew. Chem. Int. Ed. Engl., 48, 5657-5660 (2009)). A typical peak Hall voltage caused by a passing magnetic object is ~1 mV with a duration of 20 μs. The output impedance of the Hall sensors was 100Ω.

Example 2: Characterization of Magnetic Cytometer for Detection of Target Analyte Presence The capacity of the magnetic cytometer for in-flow detection was characterized using magnetic beads as target objects. The same magnetic cytometer used for Example 1 was used for these experiments. FIG. 13A shows the measured Hall signal ($V_H$) as a single 8 μm diameter magnetic bead (UMC4F; BangsLabs) in a phosphate buffer solution (PBS) passed over a Hall effect sensor. The duration of the peak corresponds to the flight time ($\approx$20 μs) of the bead over the sensor, and was utilized to estimate the flow velocity ($\approx$0.5 m/s). With the external magnetic field ($B_0$) applied out-of-plane only a single peak was observed. When the $B_0$ direction was switched to in-plane, two identical peaks with opposite phase were observed (see FIG. 13B), confirming that the signals originated from the magnetic bead. We opted to use the out-of-plane $B_0$ configuration, as it can induce larger Hall voltages and simplify data analysis by producing a single event per cell.

Example 3: Measurements of Target Analyte Position

We further investigated the use of an array of μHall array to perform accurate magnetic measurements, invariant to the position of the magnetic moment across the fluidic channel. Using the device described in Example 1, a fluid sample containing magnetic beads (UMC4F; BangsLabs) was passed over the Hall sensors. The peak amplitudes from all eight Hall sensors were collected and fitted to a numerical model. The analysis yielded the magnetic moment (m) of the bead as well as its lateral and vertical position above the array. The estimated m (0.81 A·μm$^2$) by the magnetic cytometer agreed well with the previously reported value (0.88 A·μm$^2$) (see, e.g., Shevkoplyas, S. S., Siegel, A. C., Westervelt, R. M., Prentiss, M. G. & Whitesides, G. M., "The force acting on a superparamagnetic bead due to an applied magnetic field," Lab Chip 7, 1294-1302 (2007)).

In addition, the mean Hall voltage $V_H$ over the array was found to be less dependent on the vertical position of a magnetic object, as the array captures most of the magnetic flux emanating from the object. The mean Hall voltage thus serves as an effective metric in comparing the relative MNP-load in target objects. Indeed, when the same type of magnetic beads but with different diameters (a=8 μm (UMC4F); a=3 μm, (UMC3F)) were separately detected by the magnetic cytometer the measured mean values of $V_H$ were proportional to the bead volume, reflecting uniform magnetic contents in these beads (see FIG. 11). When the mixture of beads was profiled, two distinct peaks in the mean Hall voltage could be observed even at high detection rate (about $10^5$ beads/second). Thus, the new devices can be used to easily distinguish between target analytes of different sizes

Example 4: High-Throughput Cellular Profiling

We next evaluated the capacity of the magnetic cytometer for molecular profiling on mammalian cells. To achieve effective cellular labeling with magnetic nanoparticles (MNP), we utilized a two-step bio-orthogonal approach (BOND-2) that is based on the cycloaddition between a 1,2,4,5-tetrazine (Tz) and a trans-cyclooctene (TCO) (see, e.g., Haun, J. B., Devaraj, N. K., Hilderbrand, S. A., Lee, H. & Weissleder, R., "Bioorthogonal chemistry amplifies nanoparticle binding and enhances the sensitivity of cell detection," Nat. Nanotechnol., 5, 660-665 (2010)).

Cells were first targeted with TCO-conjugated antibodies. Once bound to cellular targets, the TCO-antibodies served as a scaffold to couple multiple Tz-modified MNPs. The fast, chemoselective reaction between Tz and TCO has been shown to provide highly efficient and selective MNP coupling in biological samples. BOND-2 results in higher (>300%) MNP loading on target cells than direct antibody-MNP conjugates (see, e.g., Haun, J. B., Devaraj, N. K., Hilderbrand, S. A., Lee, H. & Weissleder, R., "Bioorthogonal chemistry amplifies nanoparticle binding and enhances the sensitivity of cell detection," Nat. Nanotechnol., 5, 660-665 (2010)) and thereby enhances the detection sensitivity of the magnetic cytometer.

Cell Culture

Human cancer cell lines (MDA-MB-453, MDA-MB-468, A431, SKMG3) were cultured in Dulbecco's modified essential medium (DMEM, Cellgro), supplemented with fetal bovine serum (10% FBS, Cellgro), penicillin and streptomycin (1%, Cellgro). All cell lines were maintained at 37° C. in a humidified atmosphere containing 5% $CO_2$. At confluence, cells were washed, trypsinized, and resuspended in culture media.

Tetrazine (TZ) Modification of Magnetic Nanoparticles and Transcyclooctene (TCO) Modification of Antibodies Fluorescein conjugated amine-terminated cross-linked iron oxides were prepared as previously described. The iron oxide particles were modified with 2,5-dioxopyrrolidin-1-yl 5-(4-(1,2,4,5-tetrazin-3-yl)benzylamino)-5-oxopentanoate (TZ-NHS) to create CLIO-TZ. Briefly, excess TZ-NHS was reacted with amino-CLIO in PBS containing 0.1M sodium bicarbonate, for 3 hours at room temperature. TZ-CLIO was purified using Sephadex G-50 columns (GE Healthcare).

The following monoclonal antibodies were modified with TCO: Herceptin (anti-HER2/neu), Cetuximab (anti-EGFR), anti-EPCAM (R&D Systems). Antibodies were modified with (E)-cyclooct-4-enyl 2,5-dioxopyrrolidin-1-yl carbonate (TCO-NHS). Briefly, purified antibody was reacted with TCO-NHS in 10% dimethylformamide for 3 hours at room temperature. TCO conjugated antibodies were subsequently buffer-exchanged into PBS and their concentrations determined by absorbance measurements.

In Vitro Cell Targeting and Measurement

Cancer cells were trypsinized and labeled with TCO conjugated antibodies (10 μg/mL) in PBS with 0.5% bovine serum albumin (BSA, Sigma) for 45 minutes at 4° C. Following washing and centrifugation, cells were labeled with FITC conjugated CLIO-TZ at room temperature for 30 minutes. After twice washing by centrifugation, FITC fluorescence was assessed using a LSRII flow cytometer (Becton Dickinson). Mean fluorescence intensity was determined using FlowJo software, and biomarker expression levels were normalized with isotype control antibodies. Corresponding magnetic signal was registered by the Hall sensor.

Figure 14A:
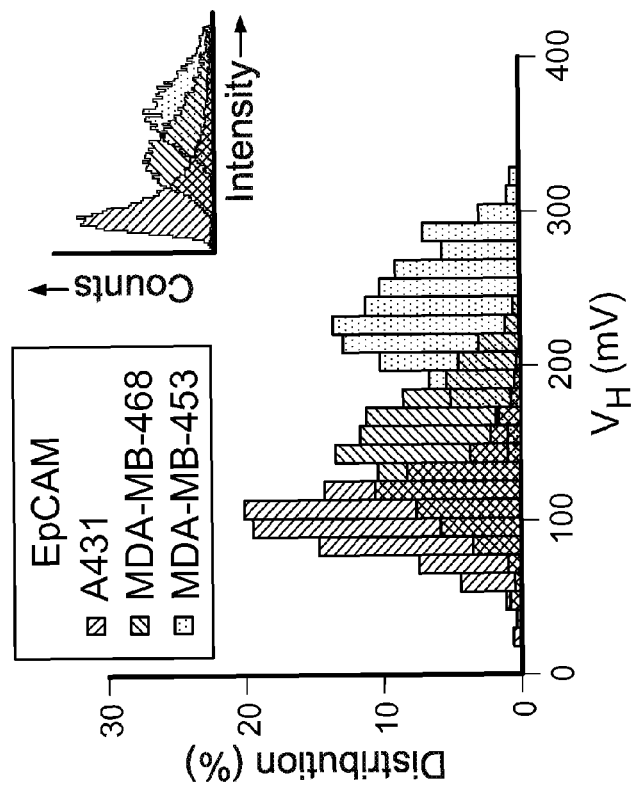
FIG. 14A is a plot of voltage distribution for measurements made of three cancer biomarkers for a single cancer cell line in a magnetic cytometer.

Using a magnetic cytometer fabricated according to the procedures described in Example 1 and cells prepared as described above, we started by screening a tumor cell line (MDA-MB-453; human breast) for three different cancer markers, HER2/neu (human epidermal growth factor receptor 2), EGFR (epithelial growth factor receptor), and EpCAM (epithelial cell adhesion molecule). Cells were separately labeled for respective markers via BOND-2. Fluorescent MNPs were used to enable direct comparison between the magnetic cytometer and flow cytometer (FCM). The profiling results by the magnetic cytometer (see FIG. 14A) showed good agreement to those by FCM (see FIG. 14A, inset), but with a notable difference. Namely, due to the lack of magnetic background in biological samples, the magnetic cytometer detected no signal (below the noise level) for the negative biomarker (EGFR for MDA-MB-453). FCM, in contrast, reported appreciable signals from autofluorescence, necessitating manual, cell type-dependent gating.

Figure 14B:
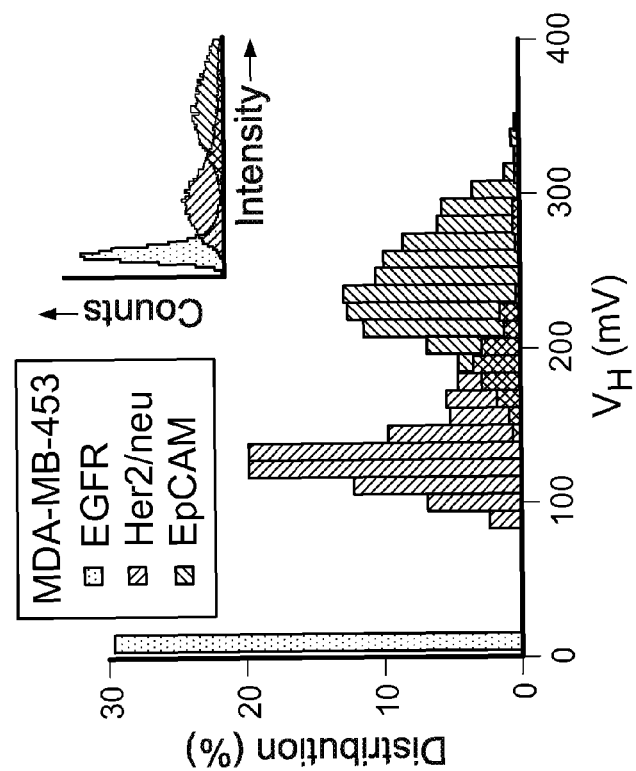
FIG. 14B is a plot voltage distribution for measurements made of a single cancer biomarker for three different cancer cell lines.
Figure 14C:
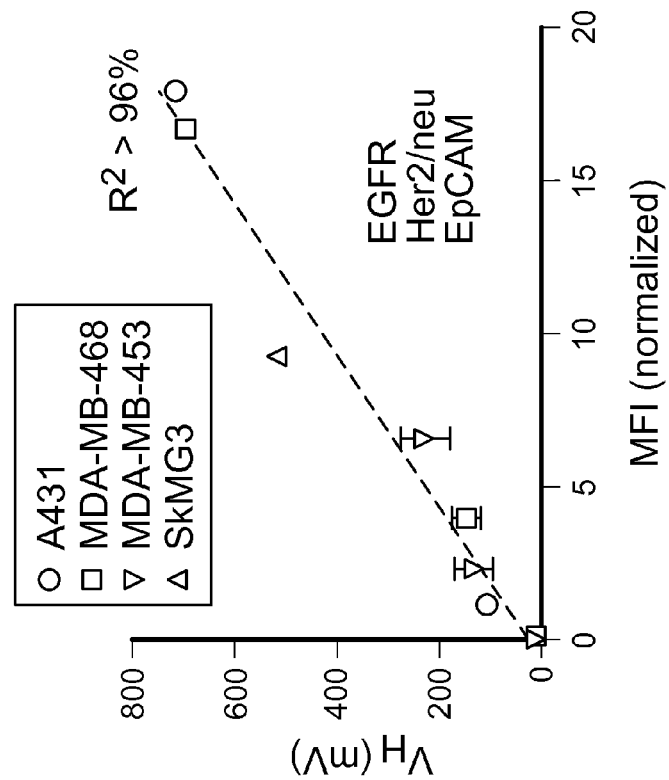
FIG. 14C is a plot of the correlation between voltage measurements made by a magnetic cytometer and by a flow cytometer for the same three biomarkers.

We further examined whether the magnetic cytometer could reliably detect different markers in different cell types. For example, FIG. 14B compares EpCAM expression level of three cell lines (A431, MDA-MB-468, MDA-MB-453). Although the cell size was different among cell types, the expression profiles for the mean voltage output $V_H$ from the Hall sensors matched well with those by FCM. This could be attributed to the novel detection mechanism in the magnetic cytometer; the use of the Hall sensor array and the flow focusing enables the magnetic cytometer to detect the overall magnetic moment that is independent of cell size but is proportional to the number MNPs per cell. Consequently, when a panel of cell lines (MDA-MB-453, MDA-MB-468, A431, SKMG3) were screened for all three biomarkers (HER2/neu, EGFR, and EpCAM), we observed an excellent linear correlation (coefficient of determination $R^2 > 96\%$) between the magnetic cytometer and FCM (see FIG. 14C). The magnetic cytometer, however, has a much smaller footprint without bulky optical components and is amenable for portable operation.

Example 5: Testing Insensitivity to Background Noise

A key challenge to implementing sensitive and practical diagnostic technology is to minimize prerequisite sample preparation steps. Sample processing is typically required to reduce interference from biological media (e.g., red blood cells in optical detection) and excess sensing agents (e.g., unbound nanoparticles or fluorochrome). We reasoned that the magnetic cytometer could obviate such steps due to both the inherent lack of magnetic signal in biological material and the magnetic cytometer's ability to select a threshold above which to detect signals. The hypothesis was tested by profiling tumor cells (MDA-MB-453) in different media, including pure buffer solution, whole blood and pure buffer solution plus magnetic nanoparticles (see FIG. 15).

Figure 15:
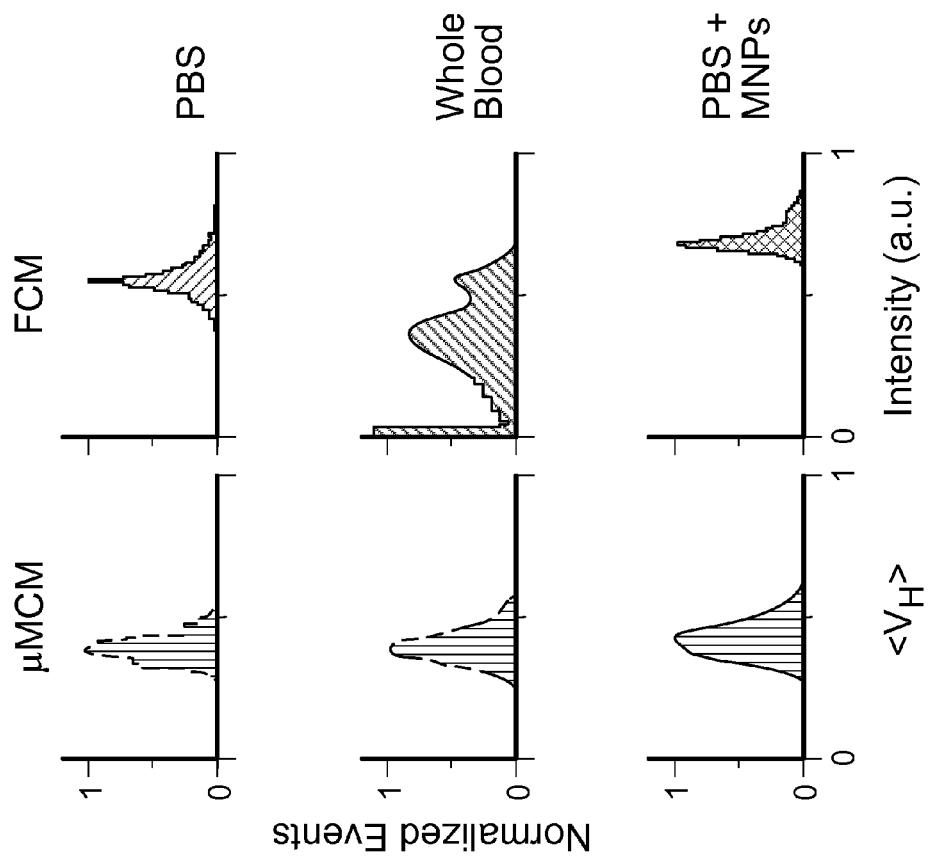
FIG. 15 is a plot of a magnetic cytometer voltage response for detecting EpCAM expressions of tumor cells in different solutions compared with flow cytometry results for the same solutions.

First, using a magnetic cytometer fabricated according to Example 1 and cells labeled according to Example 4, the effect of biological media was evaluated by comparing EpCAM expressions of tumor cells in pure buffer (FIG. 15, top panel) and in whole blood (FIG. 15, middle panel). The observed mean voltage distributions from these measurements were statistically identical ($p > 0.2$), verifying that biological noise from media is negligible in assays using the magnetic cytometer. Similar measurements with FCM, however, were limited by autofluorescence from abundant blood cells that overwhelmed the signals from target cells.

We next obtained measurements in the presence of excess MNPs, i.e., without a washing step, a requirement for FCM and most other analyses (FIG. 15, bottom panel). Even in the presence of a large amount of MNPs ($\sim 10^8$ particles/ml), the measured mean voltage distribution was similar to that measured in PBS, with a small offset (4%) in the peak position of the mean voltage $V_H$. This shift is presumably caused by the increased non-specific MNP binding from the longer exposure of cells to the particles, and could be minimized by performing measurement immediately after MNP-labeling process. Flow cytometry on the same sample yielded much more pronounced signal changes (>15%) due to the elevated fluorescence signal from the background.

Example 6: Detection and Profiling of Rare Cells in Clinical Specimen

Counting and characterizing rare cells in easily accessible biological fluid (e.g., circulating tumor cells, endothelial cells, immune cells, and stem cells) is an emergent methodology with promising potential to detect diseases at their early stage and to monitor treatment efficacy. The magnetic cytometer is a well-suited diagnostic platform for such tasks. The magnetic cytometer is capable of resolving individual target cells with few sample processing steps, and minimizes cell losses and decay of target biomarkers. Thus, the magnetic cytometer could allow for rapid, sensitive diagnostics at point-of-care settings. To demonstrate the clinical utility, we applied the magnetic cytometer to two clinically-relevant assays: detection of rare cancer cells in whole blood and assessment of longitudinal drug response in solid tumor.

Figure 16:
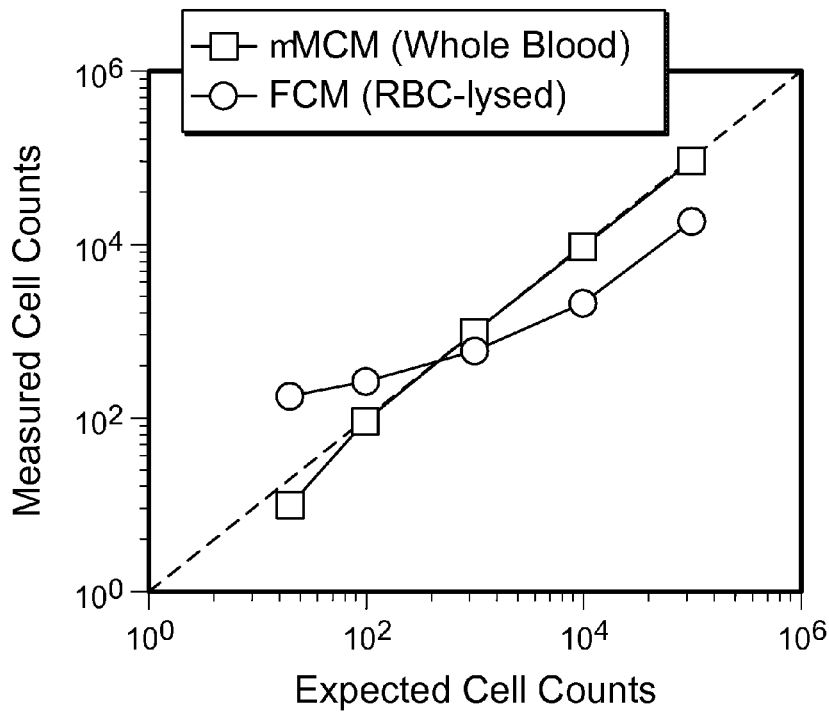
FIG. 16 is a plot of measured cancer cell counts versus expected cancer cell counts for experiments performed using a magnetic cytometer and flow cytometry.

Cancer cells were prepared as explained in Example 4. Using a magnetic cytometer prepared according to Example 1, the blood was passed through the fluidic channel of the magnetic cytometer and the voltage signals from the Hall effect sensors were recorded. FIG. 16 summarizes the cancer detection in whole blood. The counting results were in excellent agreement with the expected cell numbers (coefficient of determination $R^2 > 99.9\%$), and displayed very large dynamic ranges ($10$-$10^{-5}$ cells). Notably, the magnetic cytometer accurately detected as few as 20 cancer cells amongst the vast background of host cells ($\sim 10^6$ white blood cells, $\sim 10^9$ red blood cells). The lower detection limit was not set by magnetic cytometer, but by the logistics of very scant sample preparation.

Similar detection by FCM however, required the lysis of red blood cells (RBC) and showed a considerable discrepancy in the results, depending on the number of cells in the sample. At high cell numbers ($>10^3$ tumor cells), the error in the measurement was caused by false negatives from cell loss; at low cell numbers ($<10^3$) false positives were dominant due to the background from leukocytes. Thus, the new methods and systems tend to give more accurate results than FCM, while avoiding the need for RBC lysis.

Example 7: Monitoring the Efficacy of Drug Treatment on Tumors

We next used a magnetic cytometer fabricated according to Example 1 to monitor the efficacy of drug treatment on tumors. Xenograft tumor models were prepared by subcutaneously implanting cancer cells (A431, human epidermoid carcinoma) in mice (n=6). A431 cells ($1 \times 10^6$) were implanted into immunodeficient nu/nu mice. Tumors were allowed to grow for two weeks before mice were randomized into two groups: (1) a control group and (2) a treatment group. For the treatment group, 50 mg/kg of geldanamycin was administered intraperitoneally on a daily basis for 6 days. Geldanamycin is a benzoquinone ansamycin antibiotic that binds to Hsp90 (Heat Shock Protein 90) and inhibits its function. Once the tumor sizes reached ~1 cm in diameter, a cohort of mice (n=3) were treated daily with an intraperitoneal injection of geldanamycin. The binding of geldanamycin to hsp90 has been shown to decrease the expression of growth factor receptors (e.g., EGFR) by promoting their degradation (see, e.g., Kamal et al., Nature, 425, 407-410 (2003); Yang, S. et al., Cancer Res., 66, 6990-6997 (2006)). Briefly, A431 cells were seeded overnight and treated with drug (500 nM and 1000 nM) or vehicle (0.1% DMSO in culture medium) for two days. Cells were trypsinized and targeted with TCO conjugated EGFR antibody and coupled with magneto-fluorescent CLIO as explained in Example 4.

Control animals were given vehicle (90% saline, 10% DMSO, 0.05% Tween 20). Tumor volumes in control and treated animals were measured following 1, 2, 4, and 6 days of continuous treatment. Fine needle aspirate samples were collected on these days via a 25G needle and processed for magnetic targeting and Hall sensor measurements as before.

Flow cytometry and Hall sensor measurements were made to investigate the reduced expression of EGFR. Corresponding analyses were also done with western blotting and fluorescence microscopy. For western blotting, cell lysates were collected from A431 cells after drug treatment using radioimmuno-precipitation buffer and supplemented with protease inhibitor (Thermo Scientific). Protein lysates were resolved by sodium dodecyl sulfate polyacrylamide gel electrophoresis (SDS-PAGE), and subjected to immunodetection for EGFR expression via chemiluminescence. For fluorescence imaging, A431 cells were seeded in chamber slides (Lab-Tek) and treated with geldanamycin for two days. Cells were targeted with FITC-EGFR antibody (10 g/mL) and washed three times with PBS before fixation in 2% paraformaldehyde and permeabilization in 0.2% Triton X 100 for nuclear staining (TOPRO3, Molecular Probes). Images were taken with a fluorescence microscope (Eclipse 80i, Nikon).

Figure 17:
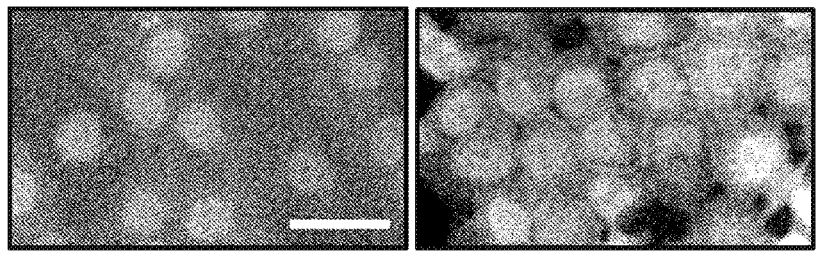
FIG. 17 is a pair of plots and a pair of microscope photographs of EGFR expression versus number of days for treated and untreated tumor cells measured using a magnetic cytometer as described herein.
Figure 17:
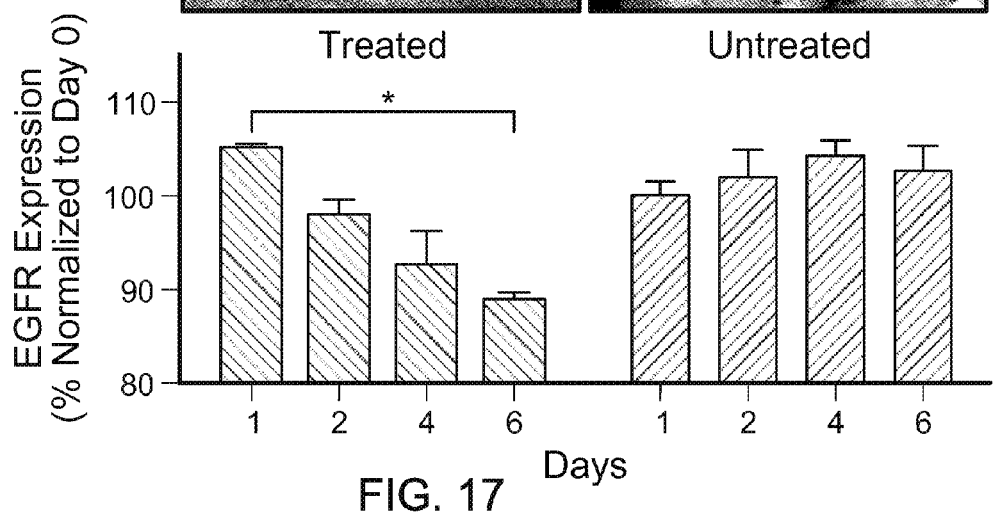

The bottom left and bottom right panels of FIG. 17 are plots of EGFR expression versus number of days for treated and untreated tumor cells, respectively, measured using a magnetic cytometer. The top left and top right panels in FIG. 17 are photographs of EpCAM expression of tumor cells that have been treated with the cancer drug and have not been treated, respectively, after 6 days. The top right panel in FIG. 17 is a photograph of tumor cells that have not been treated with the cancer drug after 6 days. With prolonged medication, a progressive decrease in EGFR expression in tumor cells was observed in the treatment group (p<0.05), whereas the expression level remained unchanged among untreated mice (see bottom left and bottom right panels in FIG. 17).

The drug also led to suppressed tumor growth in the treated cohort at later time points. The magnetic cytometer considerably facilitated this longitudinal monitoring by 1) reporting biomarker expression per cell without the need to normalize via an independent cell count, and 2) allowing for detection in small numbers of cells (~1,800 tumor cells per aspirate) in native samples.

Example 8: Multiplexed Detection of Biomarkers

Detecting multiple biomarkers in one sample is also an important and highly desirable task for diagnosis and prognosis of complex diseases. To demonstrate multiplexed biomarker detection, we labeled cells with different types of magnetic particles, each type of magnetic particle targeting a different biomarker. FIG. 18B is a schematic of an example magnetic cytometer 1800 demonstrating this concept. In particular, a target cell 1802 is labeled with three different magnetic particles 1806, 1807 and 1808. The total magnetic moment m of each cell was measured by Hall effect sensors 1804 at several different magnetization fields $B_N$ (where N=1, 2, or 3), while the cell flowed through a fluidic channel. Using the measured magnetic responses and the known magnetic properties of the magnetic particles, the number of each magnetic particle type per cell were calculated.

In particular, using a magnetic cytometer fabricated according to Example 1, we screened MDA-MB-468 cancer cells for the expression of multiple known cancer biomarkers (HER2/neu, EGFR, and EpCAM). The magnetic particles used to label the cells were manganese-doped ferrite ($MnFe_2O_4$) magnetic nanoparticles of different sizes (10 nm, 12 nm and 16 nm). Each type of magnetic nanoparticle assumed a unique magnetization response due the size difference. FIG. 18A is a plot of the magnetization response for the different magnetic particles. As shown in FIG. 18A, the 16 nm magnetic $MnFe_2O_4$ nanoparticles have a lower magnetization response for negative magnetic fields than the 12 nm and 10 nm diameter $MnFe_2O_4$ magnetic nanoparticles, but the 16 nm particles have a higher magnetization response than the 12 nm and 10 nm particles for positive magnetic fields.

The 12 nm $MnFe_2O_4$ particles have a magnetization response that is less than the 10 nm particles for negative magnetic fields, but a greater magnetization response than the 10 nm particles for positive magnetic fields. The 10 nm $MnFe_2O_4$ particles have a greater magnetization response than either the 12 nm or 16 nm particles for negative magnetic fields, but a lower magnetization response than either the 12 nm or 16 nm particles for positive magnetic fields. Labeling of the cancer cells was performed using a two-step labeling method. HER2/neu was labeled with 12 nm $MnFe_2O_4$ via the 1,2,4,5-tetrazine (Tz) and trans-cyclooctene (TCO) reaction. EGFR was labeled with 10 nm $MnFe_2O_4$ using the biotin-avidin-biotin reaction. EpCAM was labeled with 16 nm $MnFe_2O_4$ using the cyclodextrin-adamantine reaction.

The magnetic moments of cells at different magnetic field strengths (B) were then measured using the Hall effect sensors of the magnetic cytometer, and the level of each marker was calculated using equations (1)-(3) described above. From the measured magnetic moments ($m_1$, $m_2$, $m_3$) and the known magnetization curves ($L_a$, $L_b$, $L_c$), the number of each particle ($N_a$, $N_b$, $N_c$) can be calculated. FIG. 18C is a plot of the magnetization curve $V_H$ vs the applied field B for cells labeled for all three cancer biomarkers are plotted. The magnetization curve is fit with a sum of magnetization curves ($L_a$, $L_b$, $L_c$) allowing the expression level of the three biomarkers to be calculated ($N_a$, $N_b$, $N_c$).

Figure 18D:
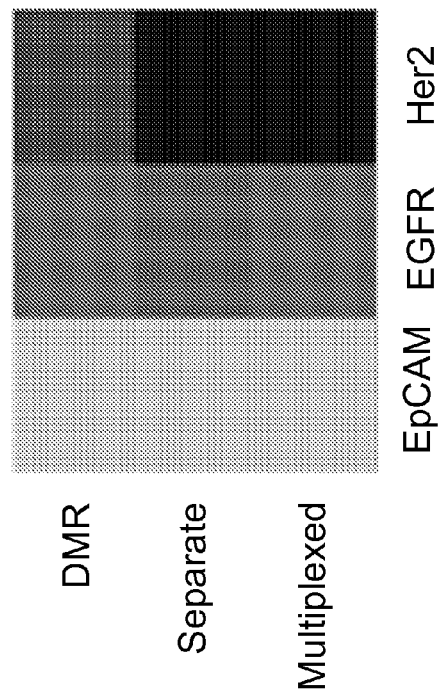
FIG. 18D is a plot of the relative expression level of the different biomarkers as measured using magnetic cytometry multiplexing, diagnostic magnetic resonance, and magnetic cytometry measurements of cancer cells labeled with a single type of magnetic particle.
Figure 18C:
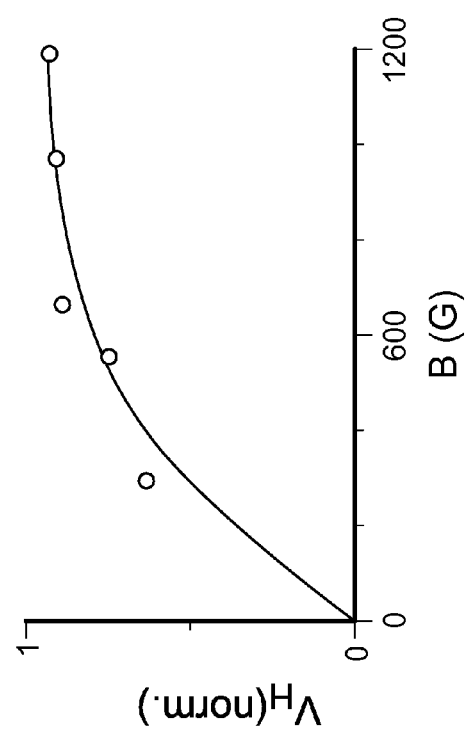
FIG. 18C is a plot of voltage output for a Hall effect sensor versus magnetic field strength.

FIG. 18D is a heat map that compares the relative expression levels measured using diagnostic magnetic resonance (DMR), separate measurements with the Hall sensor, and with the multiplexed method described above. The lighter regions indicate lower biomarker expression relative to the darker regions. As shown in the heat map, the different diagnostic techniques show good agreement. So-called "separate measurements" are measurements of cancer cells labeled with a single type of magnetic particle for each biomarker using the Hall effect sensors in place of multiple biomarkers being bound to each cell.

Example 9: Individual Bacteria Detection

We used the Hall effect cytometer to measure single, magnetically tagged bacterium directly in clinical specimens with minimal sample processing. We demonstrated the clinical utility of the Hall effect cytometer by enumerating Gram-positive bacteria using a two-step bio-orthogonal labeling procedure. In this strategy, bacterial targets were first labeled with affinity ligands modified with transcyclooctene (TCO), and magnetic nanoparticles modified with 1,2,4,5-tetrazine (Tz) were then applied. The magnetic nanoparticles were thus coupled to the labeled bacterial targets via a cycloaddition reaction between Tz and TCO. FIG. 19a illustrates an example of the assay scheme. A numerical model also was constructed to describe the spatial response of the Hall effect sensors to the magnetic moments of passing bacteria.

This method is not only fast and modular, but allows detection of a variety of different bacterial species since affinity ligands for different targets can be prepared separately, and a generic magnetic particle type can be used for labeling. Additionally, this method increases magnetic particle binding onto targets, because the affinity ligands have multiple TCO tags, which provide multiple binding sites for magnetic particles. Indeed, compared to using direct ligand-magnetic nanoparticle conjugates, this two-step method can result in much higher (>600%) magnetic nanoparticle loading onto target cells. In addition, compared to culture tests (~10 bacteria), the assay time was 50-times faster.

Simulation of Individual Bacteria Detection Using Hall Effect Sensing

Figure 21A:
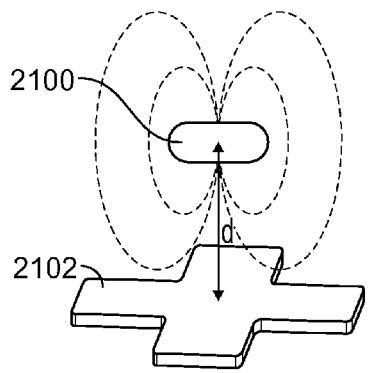
FIG. 21A is a schematic that illustrates the arrangement of a dipole relative to a Hall effect sensor.

A numerical model was constructed to describe the spatial response of the Hall effect sensors to the magnetic moments of passing bacteria. Simulations were performed in MATLAB® from Mathworks®. A magnetically labeled bacterium was approximated as a dipole moment located at the centroid of the cell. FIG. 21A is a schematic that illustrates the arrangement of the dipole 2100 relative to the Hall effect sensor 2102, in which d corresponds to the distance from the surface of the Hall effect sensor to the center of the bacterium.

Figure 21B:
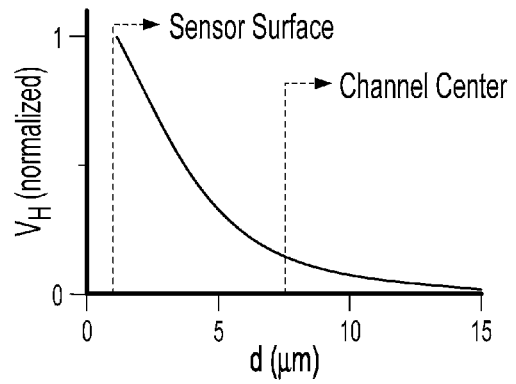
FIG. 21B is a plot of Hall voltage versus distance to a surface of a Hall effect sensor.

The magnetic field, $B_\perp$, normal to the surface of the sensor facing the fluidic channel and produced by the magnetic dipole at a specific position (x, y, z) was calculated analytically. The Hall voltage $V_H$ was then obtained for a given bias current I, by integrating $B_\perp$ over the area of the Hall effect sensor. This numerical model was used to determine the change in $V_H$ measured by the Hall effect sensor as the dipole moved away from the sensor surface. The $V_H$ signal was thus observed to drop off as the distance d increased (see FIG. 21b), showing an $r^{-3}$ dependency. For d<2 μm, the signal leveled off as most of the magnetic flux from the dipole was captured by the Hall effect sensor.

Figure 21C:
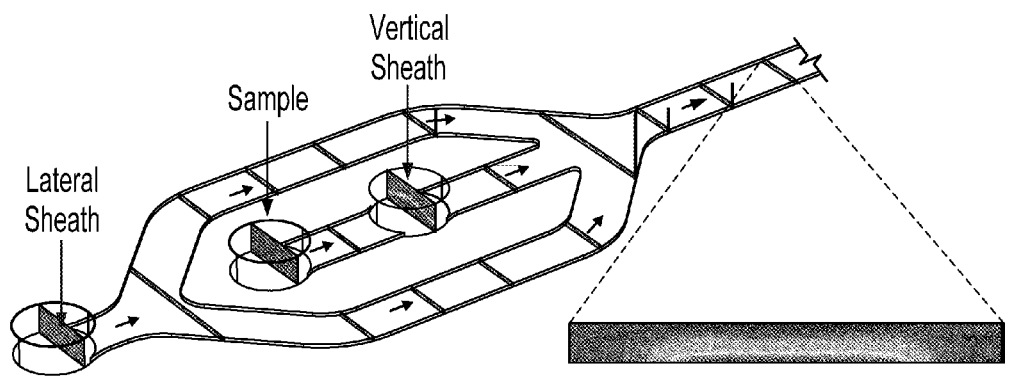
FIG. 21C is a schematic that illustrates a design of flow focusing structure used to bring pathogens close to a Hall effect sensor surface.

The fluidic channel design was iteratively optimized through finite element simulations until the sample flow could be confined within 2 μm above the sensor surface. The final implemented structure measured 200 μm wide and 15 μm high, and could operate under a flow rate of up to 2 ml/hour. FIG. 21c is a schematic that illustrates the design of the flow focusing structure used to bring pathogens close to the Hall effect sensor surface. With hydrodynamic focusing, bacteria entering the chip though the sample input port were pushed to the bottom of the channel by the vertical sheath flow (having a flow rate $S_V$) and focused towards the center of the channel by the lateral sheaths (having flow rates $S_L$). The finite-element simulation shows the focusing of bacteria to a region of ~100 μm×7.5 μm, within a physical channel measuring 200 μm×15 μm. The flow rates were: $S_V$=3S and $S_L$=8S, where S is the sample flow rate. The numerical simulation showed that the $V_H$ was >1000-fold larger for a bacterium placed on the sensor surface (d=0.5 μm) than for a bacterium placed at the center of the microfluidic channel (d=7.5 μm)

Experimental Detection of Individual Bacteria

The magnetic cytometer device was constructed as described above in Example 1. As explained in that example, each Hall effect sensor (of eight total sensors arranged in an overlapping 2×4 array) was AC coupled to the preamplifier through the high-pass filter ($f_{3dB}$=500 Hz). The active area of each sensor was about 8×8 μm². A cascaded amplifier conditioned the signal, with a gain of 30×30. The signal was then digitized (at about 2.5×10⁶ samples/s) and analyzed. A typical value for the bias current was about 2 mA. The external magnetic field ($B_0$~0.5 T) was produced by a neodymium magnet (~1 cm³ in size) attached below the chip. The sample and sheath flow were delivered to the chip via three independent syringe pumps.

Figure 20A:
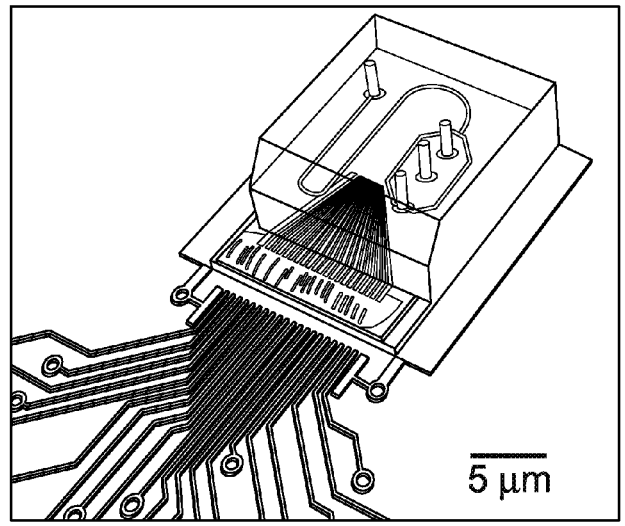
FIG. 20A is a photograph of a magnetic cytometer device.
Figure 20B:
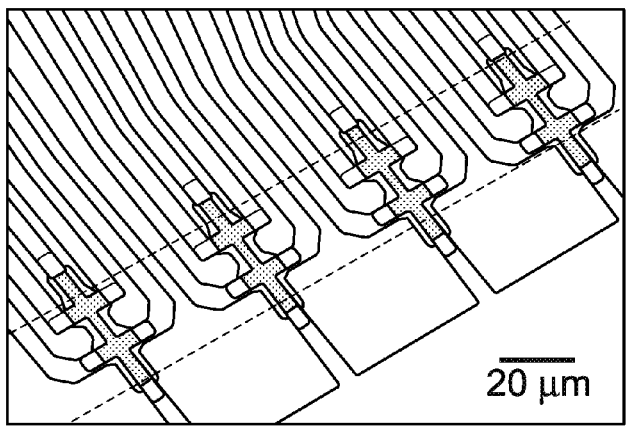
FIG. 20B is a photograph of Hall effect sensors.

FIG. 20A is a photograph of the magnetic cytometer device that includes an array of Hall effect sensors incorporated onto a semiconductor substrate with the polydimethylsiloxane (PDMS) microfluidics directly on top. FIG. 20b is a photograph of the Hall effect sensors arranged in the overlapping 2×4 array. To stream individual bacteria near to the Hall sensors, we used a two-stage flow focusing structure, as shown in FIG. 21c. Cells were confined in the vertical direction, towards the bottom of the fluid channel, via a vertical sheath flow, and directed laterally towards the center of the fluid channel via coplanar sheath flows.

Labeling agents were prepared as follows. Vancomycin, an antibiotic that binds to d-Ala-d-Ala moieties in Gram-positive bacterial membranes, was used as the labeling agent. The antibiotic was derivatized with trans-cyclooctene (TCO) to provide a facile handle for coupling with tetrazine modified magnetic nanoparticles (Tz-MNPs). To synthesize Trans-cyclooctene-modified vancomycin (vanc-TCO), 8.4 mg of vancomycin (Sigma-Aldrich) in dimethylformamide (DMF) was added to a solution of trans-cyclooctene N-hydroxy-succinimidyl ester (TCO-NHS, 4 mg) and trethylamine (58 μmol) in DMF, and reacted for 6 hours. The product was then analyzed using high performance liquid chromatography (HPLC; Waters). Further details on the synthesis of vanc-TCO can be found in Chin et al., Lab Chip, issue 7, p. 41 (2007).

Tetrazine conjugated magnetic nanoparticles (Tz-MNP) were prepared as follows. The magnetic nanoparticles used in the experiment included an iron oxide (($Fe_2O_3$)$_m$ ($Fe_3O_4$)$_n$) core and were synthesized to have a shell of crosslinked dextran, which produced a hydrodynamic diameter of about 21 nm. Each magnetic particle had 8 fluorescein molecules and 22 free amine groups on its surface. Further details on the synthesis of the magnetic particles can be found in Enserink, Science, issue 294, p. 1266 (2001).

For preparation of Tz-MNPs, tetrazine-N-hydroxysuccinimide (Tz-NHS) dissolved in 1 volume of dimethyl sulfoxide (DMSO) was added, in 500 molar excess to MNPs, in 9 volume of phosphate buffered saline (PBS) containing 10 mM sodium bicarbonate, and reacted at room temperature for 4 hours. Unreacted Tz-NHS was removed using centrifugal filters (Amicon from GE Healthcare). Further details on preparing Tz-NHS can be found in Chin et al., Nat. Med, vol. 17, page 1015 (2011).

Bacteria for the experiments were purchased from American Type Culture Collection (ATCC; Manassas, Va.). The following media were used for suspension culture of each bacterial species: *Staphylococcus aureus* (#BAA-1721) in *Staphylococcus* broth (BD Biosciences), *Enterococcus faecalis* (#29212) in tryptic soy broth (BD Biosciences) containing 5% defibrinated sheep blood (Hemostat Laboratories), *Micrococcus luteus* (#147) in nutrient broth (BD Biosciences), *Pseudomonas aeruginosa* (#142) and *Klebsiella pneumoniae* (#BAA-2146) in tryptic soy broth, and *Moraxella catarrhalis* (#8176) in brain heart infusion broth (Sigma-Aldrich).

Magnetic labeling of bacteria was performed according to a previous study with slight modifications. Bacteria in culture media were first washed with PBS containing 2% fetal bovine serum and 1 mg/ml bovine serum albumin (PBS++). For labeling, bacterial cells were added with vanc-TCO (20 µM) and incubated at room temperature for 30 min. After washing 3 times with PBS++, Tz-MNP was added (50 µg/ml) and incubated at room temperature for 40 minutes. Unreacted MNPs were removed by washing 3 times with PBS++, and fixed in 10% paraformaldehyde for 20 minutes. Flow cytometry was performed using LSRII (BD Biosciences).

Figure 19B:
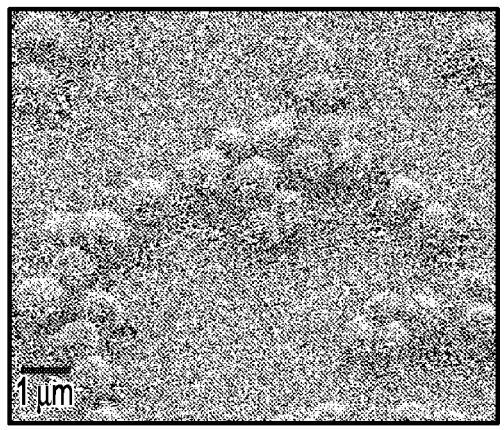
FIG. 19B is a photograph that shows an example of *Staphylococcus aureus*.
Figure 19C:
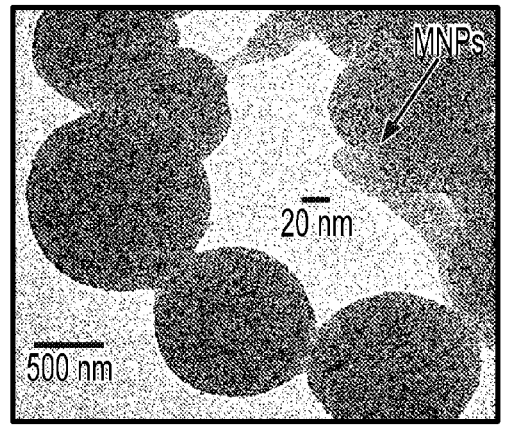
FIG. 19C is a transmission electron microscopy photograph of *Staphylococcus aureus* labeled with magnetic particles.
Figure 19D:
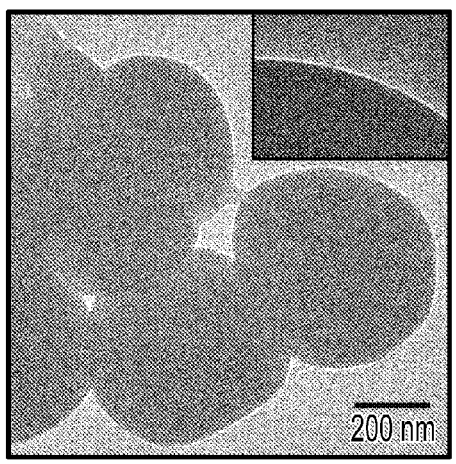
FIG. 19D is a transmission electron microscopy photograph of control samples of *Staphylococcus aureus*.

FIG. 19B is a photograph that shows an example of *Staphylococcus aureus* (*S. aureus*). The average diameter of *S. aureus* is about 1 µm. FIG. 19C is a transmission electron microscopy photograph of *S. aureus* labeled with vanc-TCO and bound to Tz-MNPs, as described above. The inset in FIG. 19C shows the MNPs bound to the bacterial membrane. The concentration of particles on the bacterial surface was about $10^5$ nanoparticles per cell. Magnetic nanoparticle loading without vanc-TCO incubation, however, was negligible, thus demonstrating the high specificity of the bioorthogonal labeling procedure. FIG. 19D is a transmission electron microscopy photograph of control bacterial samples (*S. aureus*) that were prepared without pre-targeting with vanc-TCO, and showed negligible particle binding following incubation with Tz-MNP.

Figure 21D:
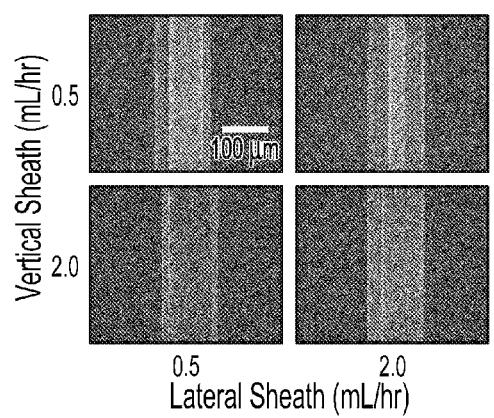
FIG. 21D is a fluorescence micrograph of hydrodynamic focusing.

The 2×4 array of Hall effect sensors in the magnetic cytometry device enabled more accurate bacterial counting, since it ensured that each bacterium passed over at least two Hall effect sensors. Detection accuracy was further enhanced by averaging the Hall voltages from all eight sensors. The mean Hall voltage ($\langle V_H \rangle$) was proportional to the total magnetic moment (m) of a single passing magnetic object, and independent of its size. Compared to mammalian cancer cells, however, bacteria are assumed to have an approximately 100-fold lower m. This is because bacteria have a much smaller surface area (diameter~1 µm) than mammalian cells (diameter~10 µm) and thus a correspondingly lower number of MNPs bind to their surface. To compensate for this loss in m, we used the two-stage flow focusing structure described above to bring bacteria nearer to the Hall effect sensors. Additionally, the use of hydrodynamic focusing allowed the physical channel to be much larger than bacteria, which in turn helped lower the fluidic resistance and reduce the risk of channel clogging. Cell confinement could be controlled by adjusting the relative flow rates of the lateral and vertical sheaths. FIG. 21d is a fluorescence micrograph of hydrodynamic focusing showing that focusing can be controlled by varying the relative flow rates between the vertical and lateral sheaths.

Figure 21E:
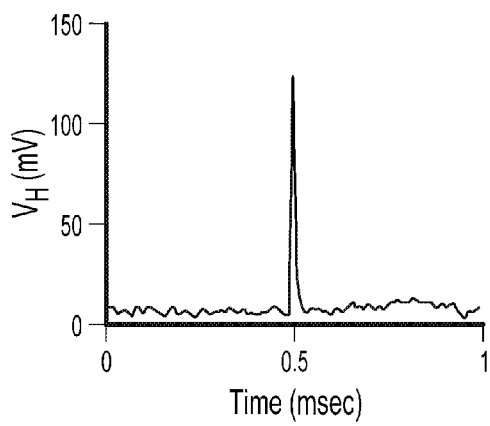
FIG. 21E is a plot of Hall voltage versus time.

Using the flow focusing structures, we were able to detect a single MNP-labeled *S. aureus* bacterium in flow by observing a distinct $V_H$ peak (having a signal to noise ratio of about 50), where the flight time of the bacterium over the sensor was 20 microseconds, and the estimated flow speed was about 1 meter/second. FIG. 21e is a plot of $V_H$ versus time, illustrating that a robust signal can be obtained from a single bacterium of *S. aureus*.

We next evaluated the analytical capacity of the magnetic cytometer by comparing the Hall effect measurements with those from flow cytometry, for which bacterial samples were prepared by labeling *S. aureus* with fluorescent magnetic nanoparticles. The measured $V_H$ distribution (from N=5,000 bacteria) obtained by the magnetic cytometer system was found to correspond well with measurements by flow cytometry and thus confirmed the accurate detection of bacterial magnetic moments by the magnetic cytometer system. FIG. 22A is a plot of Hall voltage distribution, as measured by the magnetic cytometer system. Measurements performed by flow cytometry are shown in the inset. As can be seen in FIG. 22A, the magnetic cytometer was seen to qualitatively match with measurements by flow cytometry.

Because the $V_H$ histogram obtained by the magnetic cytometer system was positioned well above the noise floor of the device (having a signal-to-noise ratio of about 5), it ensured that all bacteria in the sample would be counted. Indeed, when we used samples with known bacterial concentrations, we obtained excellent agreement with expected bacterial counts ($R^2$>97%) over a wide dynamic range ($10^1$-$10^6$ counts). FIG. 22B is a plot of the counts using the magnetic cytometer versus expected counts. The data in FIG. 22B are displayed as means (±standard error of mean) of triplicate measurements. It is possible that the deviation observed at low bacterial counts are due to errors arising from the preparation of spiked-samples. Overall, however, because the magnetic cytometer system is capable of measuring individual bacteria, the detection limit is ultimately one bacterium.

Another benefit to detection using the magnetic cytometer is that because the sensing mechanism is based on magnetic interactions, Hall measurements are robust against various biological backgrounds. Furthermore, measurements could be performed even in the presence of excess magnetic nanoparticles. Because the Hall sensors detect magnetic moments arising from a very small volume (~10 µL) above their surface, there would be on average less than 1 unbound MNP in the detection volume at any given time (for a particle concentration of $10^8$/mL). Pathogens, however, can have $10^4$-$10^6$ MNPs per cell, and thus signal arising from any unbound particles would be negligible in comparison. To test this hypothesis, we compared detection of bacteria in both pure buffer (phosphate buffer saline) and in the presence of excess magnetic nanoparticles ($10^9$ particles/ml). In doing so, we confirmed that Hall voltages from both samples were similar. FIG. 22C is a plot of Hall voltage with (shaded bar) and without (non-shaded bar) excess magnetic nanoparticles. The slight increase in $V_1$ (about 7%) observed in the presence of excess magnetic nanoparticles is presumed to be the result of longer exposure of bacteria to the magnetic nanoparticles, an effect that could be compensated for in post-data processing. In view of such background insensitivity, direct pathogen detection is possible. This capability significantly simplifies the assay procedure and minimizes the loss of rare pathogens.

To demonstrate clinical utility, we applied the magnetic cytometer to the detection of Gram-positive bacteria. The early diagnosis of such bacteria has become increasingly important with the emergence of drug resistant strains (e.g., methicillin-resistant *S. aureus*/MRSA, vancomycin-resistant enterococci, penicillin-resistant *Streptococcus pneumoniae*). The following panel of Gram-positive bacteria were tested: *S. aureus*, *Enterococcus faecalis* (*E. faecalis*) and *Micro-* coccus luteus (*M. luteus*). As a control group, the following Gram-negative species were used: *Klebsiella pneumoniae* (*K. pneumoniae*), *Moraxella catarrhalis* (*M. catarrhalis*), *Pseudomonas aeruginosa* (*P. aeruginosa*). Samples were prepared by first culturing bacteria in liquid media, and then labeled with vanc-TCO and fluorescent Tz-MNP via the two-step bioorthogonal labeling method described above. FIG. 22D is a plot of $V_H$ versus mean fluorescent intensity for the different bacteria. Both the magnetic cytometer and flow cytometry were able to reliably distinguish Gram-positive from Gram-negative species. The magnetic cytometer, however, required a far smaller sample volume (about 1 µL) than the flow cytometer (about 500 µL). Moreover, the magnetic cytometer assay time per sample was about 1 hour (30 minutes for magnetic nanoparticle labeling and 30 minutes for detection). By using different affinity ligands, the system could ultimately be adapted to detect a variety of strain-specific pathogens (e.g., by using antibodies) and bacteria (e.g., by using a Gram-staining equivalent).

By combining recent advances in magnetic nanomaterials and microelectronics, the magnetic cytometer offers advantages such as: 1) minimal sample processing, since magnetic sensing is robust against different biological backgrounds (e.g., pH, salinity, turbidity), 2) high throughput detection (e.g., $10^7$ cells/minute) and high resolution (single cell detection); and 3) simple and automatic diagnosis using a compact and self-contained device.

OTHER EMBODIMENTS

It is to be understood that while the invention has been described in conjunction with the detailed description thereof, the foregoing description is intended to illustrate and not limit the scope of the invention, which is defined by the scope of the appended claims. For example, in some implementations,

What is claimed is:
1. A target analyte detection and analysis device comprising:
 a substrate comprising a plurality of Hall effect sensors;
 a fluidic channel arranged on a surface of the substrate and extending over a detection area of the plurality of Hall effect sensors, the fluidic channel having a length along which a fluid sample flows, a width, and a height,
  wherein the plurality of Hall effect sensors is arranged in multiple rows, each row comprising multiple Hall effect sensors, and each row being located at a different longitudinal position along the length of the fluidic channel, and
  wherein the Hall effect sensors within each row of the multiple rows are laterally staggered along the width of the fluidic channel relative to Hall effect sensors within an adjacent row of the multiple rows, and
  wherein the fluidic channel comprises
   a first input port at a first end of the fluidic channel to receive the fluid sample;
   a second input port at the first end of the fluidic channel to receive a sheath fluid; and
   a third input port at the first end of the fluidic channel to receive the sheath fluid, wherein the second input port and the third input port are positioned on opposite sides of the first input port to enable the formation of a sheath flow of the sheath fluid around the fluid sample;
 a magnet arranged to generate a magnetic field in the fluidic channel;
 a plurality of flow focusing structures arranged on a top surface of the fluidic channel and configured to work in conjunction with the sheath flow to direct target analytes in the fluid sample towards the center and bottom of the fluidic channel and closer to the Hall effect sensors; and
 control electronics coupled to the plurality of Hall effect sensors, wherein the control electronics are configured to cause the device to:
  (a) detect signals from the plurality of Hall effect sensors;
  (b) determine a presence of a target analyte in the fluidic channel based on the signals; and
  (c) determine one or more of:
   (i) a size of a target analyte,
   (ii) a number of magnetic particles bound to a target analyte,
   (iii) a number of each magnetic particle type per cell,
   (iv) a density of a surface marker on a target analyte, and
   (v) a level of expression of a biomarker on the target analyte.

2. The target analyte detection device of claim 1, wherein the substrate further comprises a pseudomorphic high electron mobility transistor (PHEMT) heterostructure.

3. The target analyte detection device of claim 1, wherein each Hall effect sensor, of the plurality of Hall effect sensors, comprises a first pair of electrodes and a second pair of electrodes, and wherein the electronic processor is configured to:
 detect a signal from the first pair of electrodes; and
 supply current to the Hall effect sensor through the second pair of electrodes.

4. The target analyte detection device of claim 1, wherein the substrate further comprises an insulating layer sandwiched between the plurality of Hall effect sensors and the fluidic channel.

5. The target analyte detection device of claim 1, wherein the insulating layer comprises at least one layer selected from the group consisting of an $Al_2O_3$ layer, a $Si_3N_4$ layer, and a $SiO_2$ layer.

6. The target analyte detection device of claim 1, further comprising polydimethylsiloxane (PDMS) arranged on a surface of the substrate and configured to define boundaries of the fluidic channel.

7. The target analyte detection device of claim 1, wherein each of the flow focusing structures comprises a wall shaped in a chevron pattern.

8. The target analyte detection device of claim 1, wherein at least two of the Hall effect sensors are coupled in series across the width of the fluidic channel.

9. The target analyte detection device of claim 1, further comprising:
 a plurality of fluidic channels on the substrate; and
 wherein the plurality of Hall effect sensors are arranged in multiple arrays, and wherein each fluidic channel extends over a detection area of at least one array.

10. The target analyte detection device of claim 1, wherein the control electronics are further operable to determine a velocity and size of the target analyte in the fluidic channel.

11. The target analyte detection device of claim 1, wherein the control electronics are further operable to determine a presence of a second target analyte in the fluidic channel based on the measured signal.

12. The target analyte detection device of claim 1, wherein the fluidic channel is configured to confine particles within a fluid sample along the width of the fluidic channel.

13. The target analyte detection device of claim 1, wherein each row of Hall effect sensors consists of a pair of Hall effect sensors, wherein a first Hall effect sensor in each pair of Hall effect sensors is electrically coupled in series to the other Hall effect sensor in the pair.

* * * * *

UNITED STATES PATENT AND TRADEMARK OFFICE
CERTIFICATE OF CORRECTION

PATENT NO. : 9,958,416 B2  
APPLICATION NO. : 14/360090  
DATED : May 1, 2018  
INVENTOR(S) : Ralph Weissleder, Hakho Lee and David Issadore Page 1 of 1

It is certified that error appears in the above-identified patent and that said Letters Patent is hereby corrected as shown below:

On the Title Page

Column 1, after "0 days." Delete "days."

In the Claims

Column 32, Line 40 Claim 5:
Delete "Claim 1," and Insert --claim 4,--

Signed and Sealed this
Twenty-eighth Day of August, 2018

Andrei Iancu
*Director of the United States Patent and Trademark Office*